United States Patent
Spence et al.

(10) Patent No.: US 9,808,283 B2
(45) Date of Patent: Nov. 7, 2017

(54) APPARATUS AND METHODS FOR CUTTING AN ATRIAL WALL

(71) Applicants: HeartWare, Inc., Framingham, MA (US); Bette Levy

(72) Inventors: Paul A. Spence, Louisville, KY (US); Landon Tompkins, Louisville, KY (US); Robert Acland, Louisville, KY (US)

(73) Assignee: HeartWare, Inc., Miami Lakes, FL (US)

( * ) Notice: Subject to any disclaimer, the term of this patent is extended or adjusted under 35 U.S.C. 154(b) by 78 days.

(21) Appl. No.: 14/560,512

(22) Filed: Dec. 4, 2014

(65) Prior Publication Data

US 2015/0223839 A1 Aug. 13, 2015

Related U.S. Application Data

(60) Provisional application No. 61/911,678, filed on Dec. 4, 2013.

(51) Int. Cl.
 *A61B 17/32* (2006.01)
 *A61B 17/34* (2006.01)
 (Continued)

(52) U.S. Cl.
 CPC ...... *A61B 17/3468* (2013.01); *A61B 17/0218* (2013.01); *A61B 17/3415* (2013.01);
 (Continued)

(58) Field of Classification Search
 CPC ............ A61B 17/3478; A61B 17/0218; A61B 17/3415; A61B 17/3494;
 (Continued)

(56) References Cited

U.S. PATENT DOCUMENTS 2,935,068 A 5/1960 Donaldson
3,195,540 A 7/1965 Waller
(Continued)

FOREIGN PATENT DOCUMENTS

FR 1514319 2/1968
WO WO 82/01644 5/1982
(Continued)

OTHER PUBLICATIONS

Antaki, J. F. et al., "An improved left ventricular cannula for chronic dynamic blood pump support," Artificial Organs, 19(7):671-675 (1995).
(Continued)

*Primary Examiner* — Richard Louis
(74) *Attorney, Agent, or Firm* — Christopher & Weisberg, P.A.

(57) ABSTRACT

A method includes coupling, at least temporarily, a support member adjacent to a target tissue. The support member is configured to support the target tissue and to define a path along which a cutting device can move. The method includes moving the cutting device along the path defined by the support member to cut and/or dilate the target tissue. In some embodiments, the method optionally includes disposing a cannula of a device within the cut defined in target tissue. The cannula is coupled to the target tissue such that a lumen defined by the cannula is in fluid communication with a volume defined at least in part by the target tissue.

14 Claims, 26 Drawing Sheets

(51) Int. Cl.
*A61B 17/02* (2006.01)
*A61B 17/00* (2006.01)
*A61M 1/10* (2006.01)

(52) U.S. Cl.
CPC ...... *A61B 17/3478* (2013.01); *A61B 17/3494* (2013.01); *A61B 2017/00247* (2013.01); *A61B 2017/0243* (2013.01); *A61B 2017/3407* (2013.01); *A61B 2017/3488* (2013.01); *A61M 1/1008* (2014.02)

(58) Field of Classification Search
CPC .... A61B 2017/3407; A61B 2017/0243; A61B 2017/00247; A61B 2017/3488; A61B 17/3468; A61M 1/1008
See application file for complete search history.

(56) References Cited

U.S. PATENT DOCUMENTS

| | | | |
|---|---|---|---|
| 3,942,535 A | 3/1976 | Schulman | |
| 4,014,317 A | 3/1977 | Bruno | |
| 4,080,958 A | 3/1978 | Bregman et al. | |
| 4,116,589 A | 9/1978 | Rishton | |
| 4,366,819 A | 1/1983 | Kaster | |
| 4,790,825 A | 12/1988 | Bernstein et al. | |
| 4,994,078 A | 2/1991 | Jarvik | |
| 4,995,857 A | 2/1991 | Arnold | |
| 5,163,954 A | 11/1992 | Curcio et al. | |
| 5,171,207 A | 12/1992 | Whalen | |
| 5,171,218 A | 12/1992 | Fonger et al. | |
| 5,190,528 A | 3/1993 | Fonger et al. | |
| 5,287,852 A | 2/1994 | Arkinstall | |
| 5,290,227 A | 3/1994 | Pasque | |
| 5,290,251 A | 3/1994 | Griffith | |
| 5,312,341 A | 5/1994 | Turi | |
| 5,338,301 A | 8/1994 | Diaz | |
| 5,344,385 A | 9/1994 | Buck et al. | |
| 5,344,443 A | 9/1994 | Palma et al. | |
| 5,449,342 A | 9/1995 | Hirose et al. | |
| 5,545,191 A | 8/1996 | Mann et al. | |
| 5,653,676 A | 8/1997 | Buck et al. | |
| 5,676,670 A | 10/1997 | Kim | |
| 5,695,471 A | 12/1997 | Wampler | |
| 5,697,936 A | 12/1997 | Shipko et al. | |
| 5,701,919 A | 12/1997 | Buck et al. | |
| 5,704,891 A | 1/1998 | Mussivand | |
| 5,711,753 A | 1/1998 | Pacella et al. | |
| 5,738,649 A | 4/1998 | Macoviak | |
| 5,741,316 A | 4/1998 | Chen et al. | |
| 5,743,845 A | 4/1998 | Runge | |
| 5,840,070 A | 11/1998 | Wampler | |
| 5,858,009 A | 1/1999 | Jonkman | |
| 5,904,666 A | 5/1999 | DeDecker et al. | |
| 5,921,971 A | 7/1999 | Agro et al. | |
| 5,924,848 A | 7/1999 | Izraelev | |
| 5,924,975 A | 7/1999 | Goldowsky | |
| 5,938,412 A | 8/1999 | Izraelev | |
| 5,941,813 A | 8/1999 | Sievers et al. | |
| 5,944,745 A | 8/1999 | Rueter | |
| 5,947,892 A | 9/1999 | Benkowski et al. | |
| 5,948,006 A | 9/1999 | Mann | |
| 5,965,089 A | 10/1999 | Jarvik et al. | |
| 5,984,857 A | 11/1999 | Buck et al. | |
| 6,001,056 A | 12/1999 | Jassawalla et al. | |
| 6,017,355 A | 1/2000 | Hessel et al. | |
| 6,116,862 A | 9/2000 | Rau et al. | |
| 6,132,363 A | 10/2000 | Freed et al. | |
| 6,186,999 B1 | 2/2001 | Chen | |
| 6,273,861 B1 | 8/2001 | Bates et al. | |
| 6,299,575 B1 | 10/2001 | Bolling | |
| 6,328,699 B1 | 12/2001 | Eigler et al. | |
| 6,350,278 B1 * | 2/2002 | Lenker .................. | A61F 2/91 623/1.12 |
| 6,354,299 B1 | 3/2002 | Fischell et al. | |
| 6,358,266 B1 | 3/2002 | Bonutti | |
| 6,406,420 B1 | 6/2002 | McCarthy et al. | |
| 6,428,464 B1 | 8/2002 | Bolling | |
| 6,471,633 B1 | 10/2002 | Freed | |
| 6,511,412 B1 | 1/2003 | Freed et al. | |
| 6,530,876 B1 | 3/2003 | Spence | |
| 6,565,536 B1 | 5/2003 | Sohn | |
| 6,579,223 B2 | 6/2003 | Palmer | |
| 6,669,708 B1 | 12/2003 | Nissenbaum et al. | |
| 6,723,039 B2 | 4/2004 | French et al. | |
| 6,808,508 B1 | 10/2004 | Zafirelis et al. | |
| 6,889,082 B2 | 5/2005 | Bolling et al. | |
| 6,926,662 B1 | 8/2005 | Aboul-Hosn et al. | |
| 6,955,175 B2 | 10/2005 | Stevens et al. | |
| 6,994,094 B2 | 2/2006 | Schwartz | |
| 6,994,666 B2 | 2/2006 | Shannon et al. | |
| 7,037,253 B2 | 5/2006 | French et al. | |
| 7,048,681 B2 | 5/2006 | Tsubouchi et al. | |
| 7,056,294 B2 | 6/2006 | Khairkhahan et al. | |
| 7,077,801 B2 | 7/2006 | Haverich | |
| 7,169,164 B2 | 1/2007 | Borillo et al. | |
| 7,214,230 B2 | 5/2007 | Brock et al. | |
| 7,273,446 B2 | 9/2007 | Spence | |
| 7,288,104 B2 | 10/2007 | Heil, Jr. | |
| 7,340,288 B1 | 3/2008 | Karicherla et al. | |
| 7,473,239 B2 | 1/2009 | Wang et al. | |
| 7,520,850 B2 | 4/2009 | Brockway | |
| 7,585,290 B2 | 9/2009 | Kathrani et al. | |
| 7,666,203 B2 | 2/2010 | Chanduszko et al. | |
| 7,766,813 B2 | 8/2010 | Spence | |
| 7,785,246 B2 | 8/2010 | Aboul-Hosn et al. | |
| 7,881,807 B2 | 2/2011 | Schaer | |
| 7,905,823 B2 | 3/2011 | Farnan et al. | |
| 8,092,364 B2 | 1/2012 | Spence | |
| 8,114,123 B2 | 2/2012 | Brenzel et al. | |
| 8,157,720 B2 | 4/2012 | Marseille et al. | |
| 8,308,715 B2 | 11/2012 | Farnan et al. | |
| 8,333,686 B2 | 12/2012 | Marseille et al. | |
| 8,333,687 B2 | 12/2012 | Farnan et al. | |
| 8,333,727 B2 | 12/2012 | Farnan | |
| 8,343,029 B2 | 1/2013 | Farnan et al. | |
| 8,394,010 B2 | 3/2013 | Farnan | |
| 8,460,168 B2 | 6/2013 | Farnan | |
| 8,465,410 B2 | 6/2013 | Marseille et al. | |
| 8,512,012 B2 | 8/2013 | Akdis et al. | |
| 8,545,379 B2 | 10/2013 | Marseille et al. | |
| 8,545,380 B2 | 10/2013 | Farnan et al. | |
| 8,607,800 B2 | 12/2013 | Thapliyal et al. | |
| 8,784,291 B2 | 7/2014 | Farnan et al. | |
| 2002/0082614 A1 | 6/2002 | Logan et al. | |
| 2002/0151761 A1 | 10/2002 | Viole et al. | |
| 2002/0173693 A1 | 11/2002 | Landesberg | |
| 2003/0069468 A1 | 4/2003 | Bolling et al. | |
| 2003/0088147 A1 | 5/2003 | Bolling et al. | |
| 2003/0139643 A1 | 7/2003 | Smith et al. | |
| 2003/0176760 A1 | 9/2003 | El Oakley et al. | |
| 2004/0147803 A1 | 7/2004 | Hegde et al. | |
| 2005/0075665 A1 | 4/2005 | Brenzel et al. | |
| 2006/0009737 A1 | 1/2006 | Whiting et al. | |
| 2007/0049787 A1 | 3/2007 | Nose et al. | |
| 2007/0106315 A1 | 5/2007 | Gregoric et al. | |
| 2007/0197855 A1 | 8/2007 | Richardson et al. | |
| 2008/0009886 A1 * | 1/2008 | Self .................... | A61B 17/122 606/142 |
| 2008/0076959 A1 | 3/2008 | Farnan et al. | |
| 2008/0076960 A1 | 3/2008 | Marseille et al. | |
| 2008/0243081 A1 | 10/2008 | Nance et al. | |
| 2009/0023975 A1 | 1/2009 | Marseille et al. | |
| 2009/0112050 A1 | 4/2009 | Farnan et al. | |
| 2009/0182188 A1 | 7/2009 | Marseille et al. | |
| 2010/0010500 A1 | 1/2010 | Beane et al. | |
| 2010/0160719 A1 * | 6/2010 | Kassab ................ | A61M 25/00 600/37 |
| 2010/0160725 A1 | 6/2010 | Kiser et al. | |
| 2010/0249490 A1 | 9/2010 | Farnan | |
| 2010/0249491 A1 | 9/2010 | Farnan et al. | |
| 2010/0249920 A1 | 9/2010 | Bolling et al. | |
| 2011/0054487 A1 | 3/2011 | Farnan | |
| 2011/0066170 A1 | 3/2011 | Farnan | |

(56) References Cited

U.S. PATENT DOCUMENTS

| | | | |
|---|---|---|---|
| 2011/0112353 A1 | 5/2011 | Farnan et al. | |
| 2011/0112632 A1 | 5/2011 | Chau et al. | |
| 2011/0137234 A1 | 6/2011 | Farnan et al. | |
| 2011/0190697 A1 | 8/2011 | Farnan | |
| 2011/0196190 A1 | 8/2011 | Farnan et al. | |
| 2011/0196191 A1 | 8/2011 | Farnan et al. | |
| 2011/0200451 A1 | 8/2011 | Lehmann et al. | |
| 2012/0004496 A1 | 1/2012 | Farnan et al. | |
| 2012/0059213 A1* | 3/2012 | Spence | A61M 1/3653 600/16 |
| 2012/0078032 A1 | 3/2012 | Spence | |
| 2012/0259157 A9 | 10/2012 | Spence | |
| 2013/0060267 A1 | 3/2013 | Farnan et al. | |
| 2013/0116715 A1 | 5/2013 | Weber | |
| 2013/0150772 A1 | 6/2013 | Farnan et al. | |
| 2013/0172661 A1 | 7/2013 | Farnan et al. | |
| 2013/0231521 A1 | 9/2013 | Farnan | |
| 2013/0310804 A1* | 11/2013 | Jabba | A61B 17/3478 604/510 |
| 2013/0317531 A1 | 11/2013 | Chanduszko et al. | |
| 2014/0107399 A1 | 4/2014 | Spence | |
| 2014/0277045 A1* | 9/2014 | Fazio | A61B 17/32001 606/170 |

FOREIGN PATENT DOCUMENTS

| | | |
|---|---|---|
| WO | WO 97/42413 | 11/1997 |
| WO | WO 99/59652 | 11/1999 |
| WO | 9962415 A1 | 12/1999 |
| WO | WO 01/80927 | 11/2001 |
| WO | WO 2005/037345 | 4/2005 |
| WO | WO 2007/047933 | 4/2007 |
| WO | WO 2008/027869 | 3/2008 |
| WO | WO 2009/045624 | 4/2009 |
| WO | WO 2009/055651 | 4/2009 |
| WO | 2010081106 A1 | 7/2010 |
| WO | WO 2012/033847 | 3/2012 |
| WO | WO 2013/022420 | 2/2013 |

OTHER PUBLICATIONS

Antaki, J. F. et al., "Development progress of the University of Pittsburgh streamliner: a mixed flow blood pump with magnetic bearings," ASAIO Journal, 46(2):194 (2000) (Abstract only).

Antaki, J. F. et al., "In vivo evaluation of the nimbus axial flow ventricular assist system: Criteria and methods," ASAIO Journal, 39:M231-M236 (1993).

Arrow International, Inc., AutoCAT™ 2WAVE™, Brochure, Arrow International, Inc. USA (2003), 4 pages.

Bachman, T. N., "Development and evaluation of the quintessential ventricular cannula," Thesis, University of Pittsburgh (2008), 71 pages.

Baird, R. J, et al., "Survey of mechanical assistance of the circulation and the present status of left-heart bypass," Canad. Med. Ass. J., 95:646-651 (1966).

Baird, R. J. et al., "Survey of mechanical assistance of the circulation and the present status of left-heart bypass," Symposium on the Mechanical Support of the Circulation, Toronto Western Hospital, Toronto, Ontario, Canada, Nov. 5, 1965 pp. 340-345.

Baird, R. J. et al., Le Support Mecanique Du Ventricule Gauche, L'Union Med. du Canada, Tome 93, pp. 258-268 (1964).

Brooks, S. G. et al., "The use of a latissimus dorsi myocutaneous flap to cover an axillobifemoral vascular prosthetic graft," Eur. J. Vasc. Surg., 3:367-368 (1989).

"Cannula-Tip Development for Minimal Invasive Pumps," Medizinische Universitate Wien, Center for Medical Physics and Biomedical Engineering as printed on Jan. 31, 2011.

Cavallaro, A. et al., "The effect of body weight compression on axillo-femoral by-pass patency," J. Cardiovasc. Surgery, 29:476-479 (1988).

Cochran, R. P. et al., "Ambulatory intraaortic balloon pump use as bridge to heart transplant," Ann. Thorac. Surg., 74:746-752 (2002).

Copeland, J. G. III, "Thromboembolism and bleeding: Clinical strategies," Ann. Thorac. Surg., 61:376-377 (1996).

Curtis, A. S. et al., "Novel ventricular apical cannula: in vitro evaluation using transparent, compliant ventricular casts," ASAIO Journal, 44:M691-M695 (1998).

Datascope, The CS100(TM) Intelligent Counterpulsation, Brochure (2003), 11 pages.

DeBakey, M. E., "The Artificial Heart", in The History of Surgery in Houston, Kenneth L. Mattox, ed., pp. 346-358 (1998).

Dennis, C. et al., "Clinical Use of a Cannula for Left Heart Bypass Without Thoracotomy: Experimental Protection Against Fibrillation by Left Heart Bypass," Annals of Surgery, 156(4):623-636 (1962).

Dennis, C. et al., "Reducation of the Utilization of the Heart by Left Heart Bypass," Circulation Research, Journal of the American Heart Association, 10:298-305 (1962).

Dennis, C. et al., "Left atrial cannulation without thoracotomy for total left heart bypass," Acta Chir Scand., 123:267-279 (1962).

El-Banayosy, A. et al., "Bridging to cardiac transplantation with the thoratec ventricular assist device," Thorac. Cardiovasc. Surg., 47:307-310 (1999).

Fraser, K. H. et al., "Computational fluid dynamics analysis of thrombosis potential in left ventricular assist device drainage cannulae," ASAIO Journal, 56(3):157-163 (2010).

Freed, P. S. et al., "Intraortic balloon pumping for prolonged circulatory support," The American Journal of Cardiology, 61(8):554-557 (1988).

Greenberg, B. et al., Effects of continuous aortic flow augmentation in patients with exacerbation of heart failure inadequately responsive to medical therapy: Results of the multicenter trial of the orqis medical cancion system for the enhanced treatment of heart failure unresponsive to medical therapy.

Gristina, A. G. et al., "Biomaterial-centered sepsis and the total artificial heart," JAMA, 259:870-874 (1988).

Helman, D. N. et al., "Left ventricular assist device bridge-to-transplant network improves survival after failed cardiotomy," Ann. Thorac. Surg., 68:1187-1194 (1999).

Jaski, B. E. et al., "Diagnosis and treatment of complications in patients implanted with a TCI left ventricular assist device," Journal of Interventional Cardiology, 8(3):275-282 (1995).

Jeevanadam, V. et al., "Circulatory assistance with a permanent implantable IABP: Initial human experience," Circulation, 106(1):I-183-I-188 (2002).

Johnson, W. C. et al., "Is axillo-bilateral femoral graft an effective substitute for aortic-bilateral Iliac/femoral graft?: An analysis of ten years experience," Annals of Surgery, 186(2):123-129 (1977).

Kawahito, K. et al., "Ex vivo phase 1 evaluation of the DeBakey/NASA axial flow ventricular assist device," Artificial Organs, 20(1):47-52 (1996).

Kawai, A. et al., "Management of infections in mechanical circulatory support devices," Cardiac Surgery: State of the Art Reviews, 7(2):413-424 (1993).

Kirklin, J. K. et al., "Mechanical circulatory support: Registering a therapy in evolution," Circ. Heart Fail., 1:200-205 (2008).

Korfer, R. et al., "Temporary pulsatile ventricular assist devices and biventricular assist devices," Ann. Thorac. Surg., 68:678-683 (1999).

Kyo, S. et al., "Percutaneous Introduction of Left Atrial Cannula for Left Heart Bypass: Utility of Biplane Transesophageal Echocardiographic Guidance for Transseptal Puncture," Artificial Organs, 16(4):386-391 (1992).

Litwak, K. N. et al., "Retrospective analysis of adverse events in preclinical ventricular assist device experiments," ASAIO Journal, 54:1-4 (2008).

Macha, M. et al., "Survival for Up to Six Months in Calves Supported With an Implantable Axial Flow Ventricular Assist Device", ASAIO Journal, 43:311-315 (1997).

Magee, T. R. et al., "Reinforced vascular grafts: a comparative study," Eur. J. Vasc. Surg., 6:21-25 (1992).

Magovern, G. J. et al., "The biopump and postoperative circulatory support," Ann. Thorac. Surg., 55:245-249 (1993).

(56) References Cited

OTHER PUBLICATIONS

Manord, J. D. et al., "Implications for the vascular surgeon with prolonged (3 to 89 days) intraaortic balloon pump counterpulsation," J. Vasc. Surg., 26:511-516 (1997).

McBride, L. R. et al., "Clinical experience with 111 thoratec ventricular assist devices," Ann. Thorac. Surg., 67:1233-1239 (1999).

Meyns, B. et al., "Proof of Concept: Hemodynamic Response to Long-Term Partial Ventricular Support With the Synergy Pocket Micro-Pump," J. Am. Coll. Cardiol., 54(1):79-86 (2009).

Morales, D. L. S. et al., "Lessons learned from the first application of the DeBakey VAD child: An intracorporeal ventricular assist device for children," The Journal of Heart and Lung Transplantation, 24(3):331-337 (2005).

Mussivand, T. et al., "Progress with the heartsaver ventricular assist device," Ann. Thorac..Surg., 68:785-789 (1999).

Nanas, J. N. et al., "A valveless high stroke volume counterpulsation device restores hemodynamics in patients with congestive heart failure and intractable cardiogenic shock awaiting heart transplantation," The Journal of Thoracic and Cardiovascular Surgery, 111(1):55-61 (1996).

Nanas, J. N. et al., "Comparison of an implanted abdominal aortic counterpulsation device with the intraaortic balloon pump in a heart failure model," J. Am College Cardiology, 7(5):1028-1035 (1986).

Nanas, J. N. et al., "Effectiveness of a counterpulsation device implanted on the ascending aorta," Trans. Am. Soc. Artif. Intern. Organs, 33:203-206 (1987).

Nanas, J. N. et al., "Hemodynamic effects of a counterpulsation device implanted on the ascending aorta in severe cardiogenic shock," Trans. Am. Soc. Artif. Intern. Organs, 34:229-234 (1988).

Nanas, J. N. et al., "Preclinical evaluation of the abdominal aortic counterpulsation device," American Heart Journal, 116(4):1003-1008 (1998).

Nishimura, K. et al., "Results of Chronic Animal Experiments with a New Version of a Magnetically Suspended Centrifugal Pump", ASAIO Journal, 44:M725-M727 (1998).

Noon, G. P. et al., "Clinical experience with the micromed DeBakey ventricular assist device," Ann. Thorac. Surg., 71:S133-S138 (2001).

Nose, Y. et al., "Can we develop a nonpulsatile permanent rotary blood pump? Yes, we can," Artificial Organs, 20(6):467-474 (1996).

Ochiai, Y. et al., "In vivo hemodynamic performance of the cleveland clinic coraide blood pump in calves," Ann. Thorac. Surg., 72:747-752 (2001).

Ozawa, K. et al., "Inflow system for long-term ventricular assist device (LVAD)," In: Transactions American Society for Artificial Internal Organs, vol. XXVI, New Orleans, Louisiana, Apr. 17-19, 1980, pp. 24-28.

Park, J. K. et al., "Intraaortic balloon pump management of refractory congestive heart failure in children," Pediatric Cardiology, 14(1):19-22 (1993).

Petition to Request Inter Partes Reexamination of U.S. Pat. No. 6,530,876, filed Dec. 19, 2011, 215 pages.

Reddy, R. C. et al., "End organ function with prolonged nonpulsatile circulatory support," ASAIO Journal, 41:M547-M551 (1995).

Rosenbaum, A. M. et al., "Intra-aortic balloon counterpulsation as a 'bridge'•to cardiac transplantation. Effects in nonischemic and ischemic cardiomy opathy," Chest, 106(6):1683-1688 (1994).

Schmid, C. et al., "Influence of inflow cannula length in axial-flow pumps on neurologic adverse event rate: Results from a multi-center analysis," The Journal of Heart and Lung Transplantation, 27(3):253-260 (2008).

Slater, J. P. et al., "Low thromboembolic risk without anticoagulation using advanced-design left ventricular assist devices," Ann. Thorac Surg., 62:1321-1328 (1996).

Sunshine Heart, Inc. Prospectus, Underwriter Wilson HTM Corporate Finance Limited (2004), 116 pages.

Takami, Y. et al., "Anatomical Consideration for an Implantable Centrifugal Biventricular Assist System", Artif. Organs 21(10):1132-1136 (1997).

Tayama, E. et al., "The DeBakey ventricular assist device: current status in 1997," Artificial Organs, 23(12):1113-1116 (1999).

Terrovitis, J. V. et al., "Superior performance of a paraaortic counterpulsation device compared to the intraaortic balloon pump," World Journal of Surgery, 27(12):1311-1316 (2003).

World Heart Corporation, World Heart, Annual Report (1998), 36 pages.

Zile, M. R. et al., "Progressive improvement in cardiac performance with continuous aortic flow augmentation (aortic flow therapy) in patients hospitalized with severe heart failure: Results of the multicenter trial of the orqis medical cancion system for the enhanced treatment of heart failure unresponsive to medical therapy (momentum)," The Journal of Heart and Lung Transplantation, 29(1):86-92 (2010).

International Search Report for PCT/US2014/068626, dated Apr. 30, 2015, 73 pages.

Supplementary Partial European Search Report dated Jun. 28, 2017, for corresponding European Application No. EP 14867008, consisting of 12 pages.

\* cited by examiner

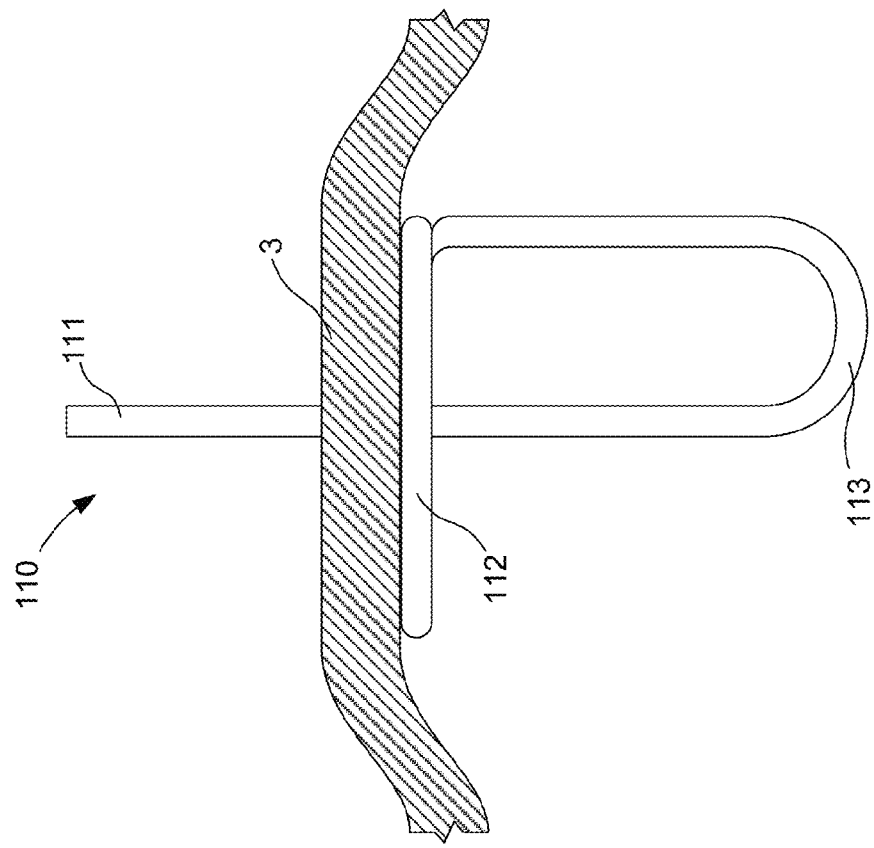
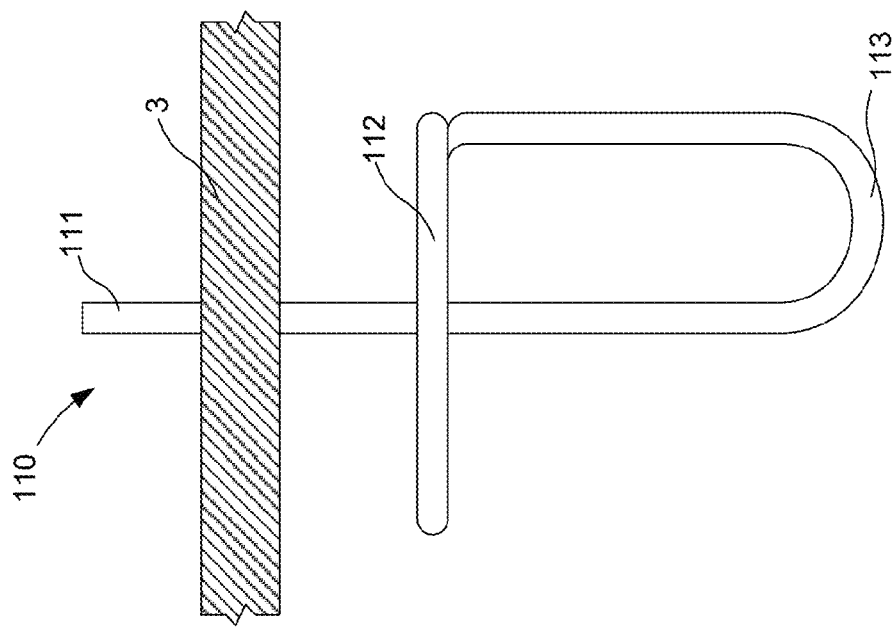

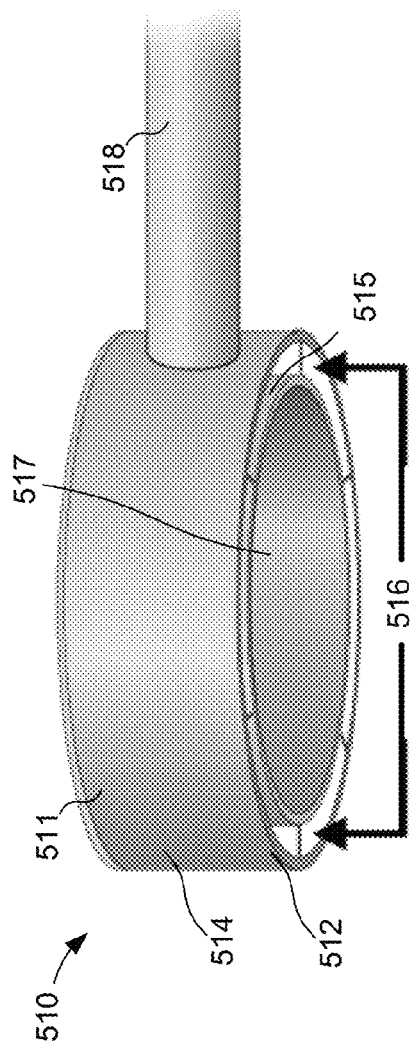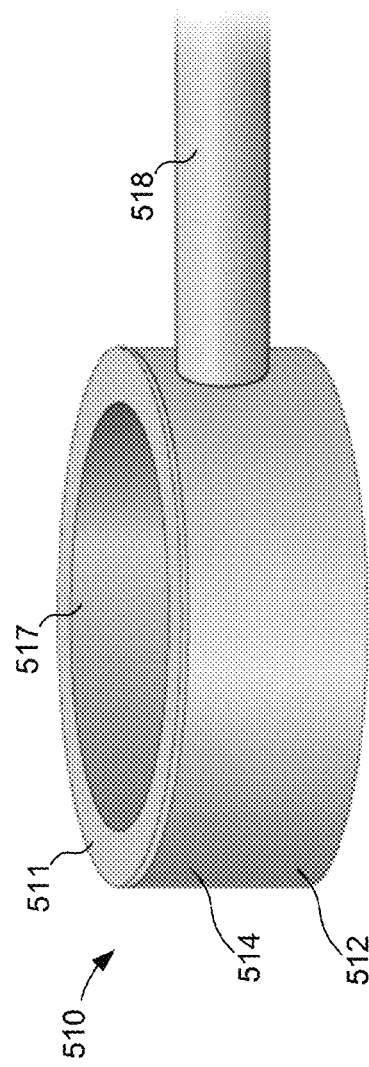

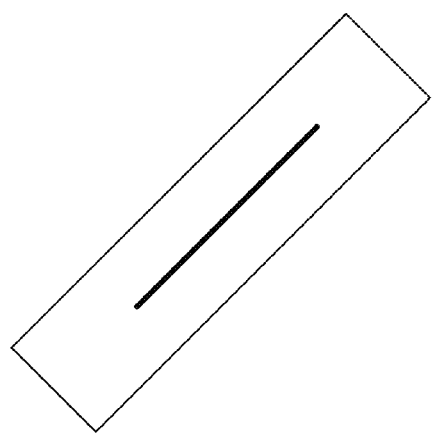
PRIOR ART
FIG. 34
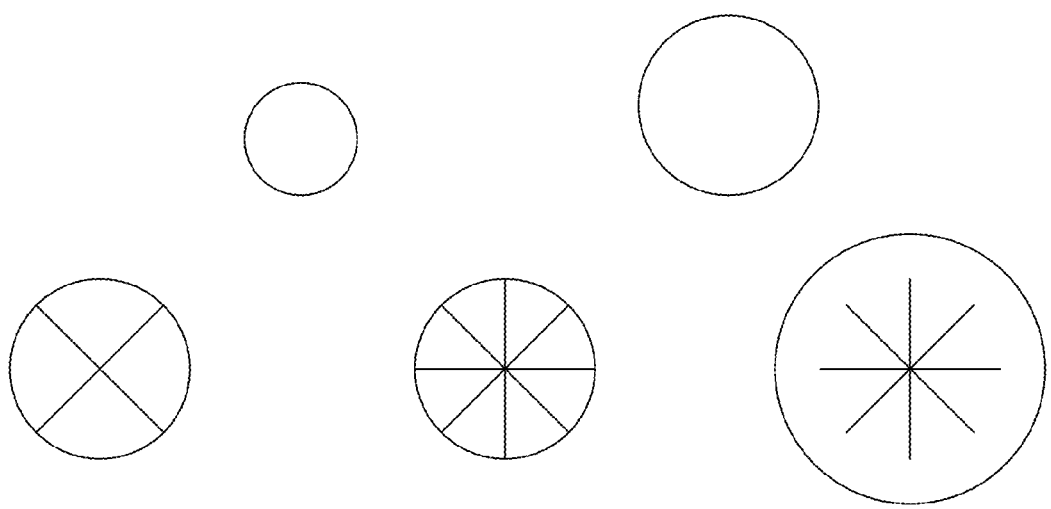
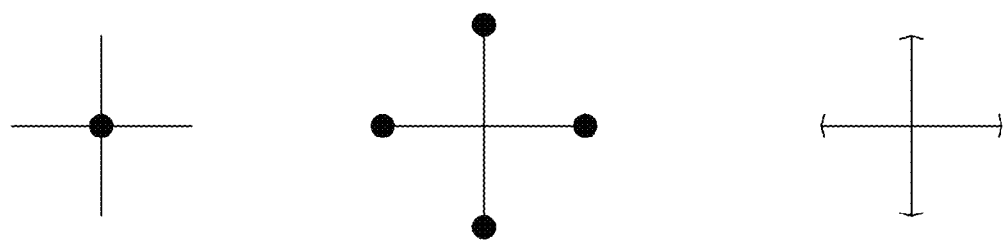
FIG. 35

APPARATUS AND METHODS FOR CUTTING AN ATRIAL WALL

CROSS REFERENCE TO RELATED APPLICATION

The present application claims priority to and benefit of U.S. Provisional Patent Application No. 61/911,678, entitled "Apparatus and Methods for Cutting an Atrial Wall," filed Dec. 4, 2013, the disclosure of which is incorporated herein by reference in its entirety.

BACKGROUND

The embodiments described herein relate generally to apparatus and methods for insertion of a cannula into target tissue, and more particularly, to cutting target tissue and inserting a cannula of a ventricular assist device into the left atrium of a heart.

The use of devices to assist the function of an ailing heart is increasing. In some instances, a ventricular assist device (VAD) can be used to partially or completely replace the function of the heart. For example, in some instances, a left ventricular assist device (LVAD) can be used to assist a heart of a patient by placing an inlet flow cannula in fluid communication with the left atrium of the heart and an outlet flow cannula in fluid communication with a portion of the aorta. The LVAD can include a pumping mechanism that can pump, transfer, draw, push, or otherwise produce a flow of blood between the inlet flow cannula and the outlet flow cannula, thereby assisting heart.

Some known methods for placing an inlet flow cannula in or at a desired location within, for example, the left atrium include advancing the inlet flow cannula through the superior vena cava (SVC) and piercing the septum between the right atrium and the left atrium. In such methods, the thickness of the septum can be sufficient to allow piercing and/or cutting thereof to provide the passage of the inlet flow cannula. Such methods, however, often include an at least partially blind piercing of the septum, which can be challenging and can result in undesirable placement of the inlet flow cannula. Some such methods can be used with imaging techniques such as, fluoroscopy and echocardiography, however, due to the distance between the insertion point and the target location of the heart and/or the torturous path of the anatomy, precision can still be difficult and the ability to apply a suitable force can be challenging.

In other instances, methods for placing an inlet flow cannula in or at a desired location within the left atrium include coupling the inlet flow cannula to the dome of the left atrium. This location can provide performance benefits because it is adjacent a wider portion of the left atrium and is remote from the left and right pulmonary veins. Coupling of the inlet flow cannula to the dome of the left atrium, however, can be complicated by the anatomy of the heart. For example, the walls of the dome of the left atrium are very thin (e.g., between 1 and 2 mm in thickness) and fragile, which can make incising the tissue difficult. Moreover, certain procedures may include dilating an incision in the atrial wall with a dilator and/or balloon catheter, for example, to accommodate the desired size of the inlet flow cannula. Dilation of certain tissue, such as the dome of the atrium can lead to tearing of the tissue and/or fracture that can extend beyond a diameter of the dilator (e.g., due at least in part on the thinness of the tissue). In addition, the interior of the atrium can be at a relatively low pressure, due to the function of the heart. Therefore, when the dome of the left atrium is pushed and/or manipulated from the outside to incise or dilate the tissue (e.g., with a scalpel or other tool), the tissue can collapse into the atrium, making a clean cut of the atrium wall difficult to achieve. In some instances, similar collapse can occur in, for example, transseptal puncture and/or a puncture through the right atrial wall.

Thus, a need exists for improved apparatus and methods for cutting target tissue and inserting a cannula of a ventricular assist device into the left atrium of a heart.

SUMMARY

Apparatus and methods for cutting target tissue and inserting a cannula of a ventricular assist device into the left atrium of a heart are described herein. In some embodiments, a method includes coupling, at least temporarily, a support member adjacent to a target tissue. The support member is configured to support the target tissue and to define a path along which a cutting device can move. The method includes moving the cutting device along the path defined by the support member to cut and/or dilate the target tissue. In some embodiments, the method optionally includes disposing a cannula of a device within the cut defined in target tissue. The cannula is coupled to the target tissue such that a lumen defined by the cannula is in fluid communication with a volume defined at least in part by the target tissue.

In some embodiments, an apparatus includes a support member configured to be transitioned between a first configuration and a second configuration. When the support member is in the first configuration, a contact portion of the support member is configured to be inserted through an organ wall from a first side of the organ wall to a second side of the organ wall. When the support member is in the second configuration, the contact portion of the support member is configured to contact the second side of the organ wall to limit movement of the organ wall. The contact portion of the support member has a first size when the support member is in the first configuration and a second size when the support member is in the second configuration, the second size being larger than the first size. The support member has a guide portion includes a surface along which a puncture member can be slidably disposed. The puncture member is configured to puncture the organ wall when moved along the surface and when the support member is in the second configuration

BRIEF DESCRIPTION OF THE DRAWINGS

FIG. 10 is a side view of the support member of FIG. 6 in a first position relative to a wall of an atrium when the support member is in the first configuration.

FIG. 11 is a side view of the support member of FIG. 6 in a second position relative to the wall of the atrium when the support member is in the first configuration.

FIGS. 21 and 22 are perspective views of a portion of a support member according to an embodiment.

FIG. 34 is a schematic illustration representing a resulting incision in a wall of an atrium using a known method of incision.

FIG. 35 shows schematic illustrations representing resulting incisions in a wall of an atrium using the cutting devices described herein.

DETAILED DESCRIPTION

Figure 1:
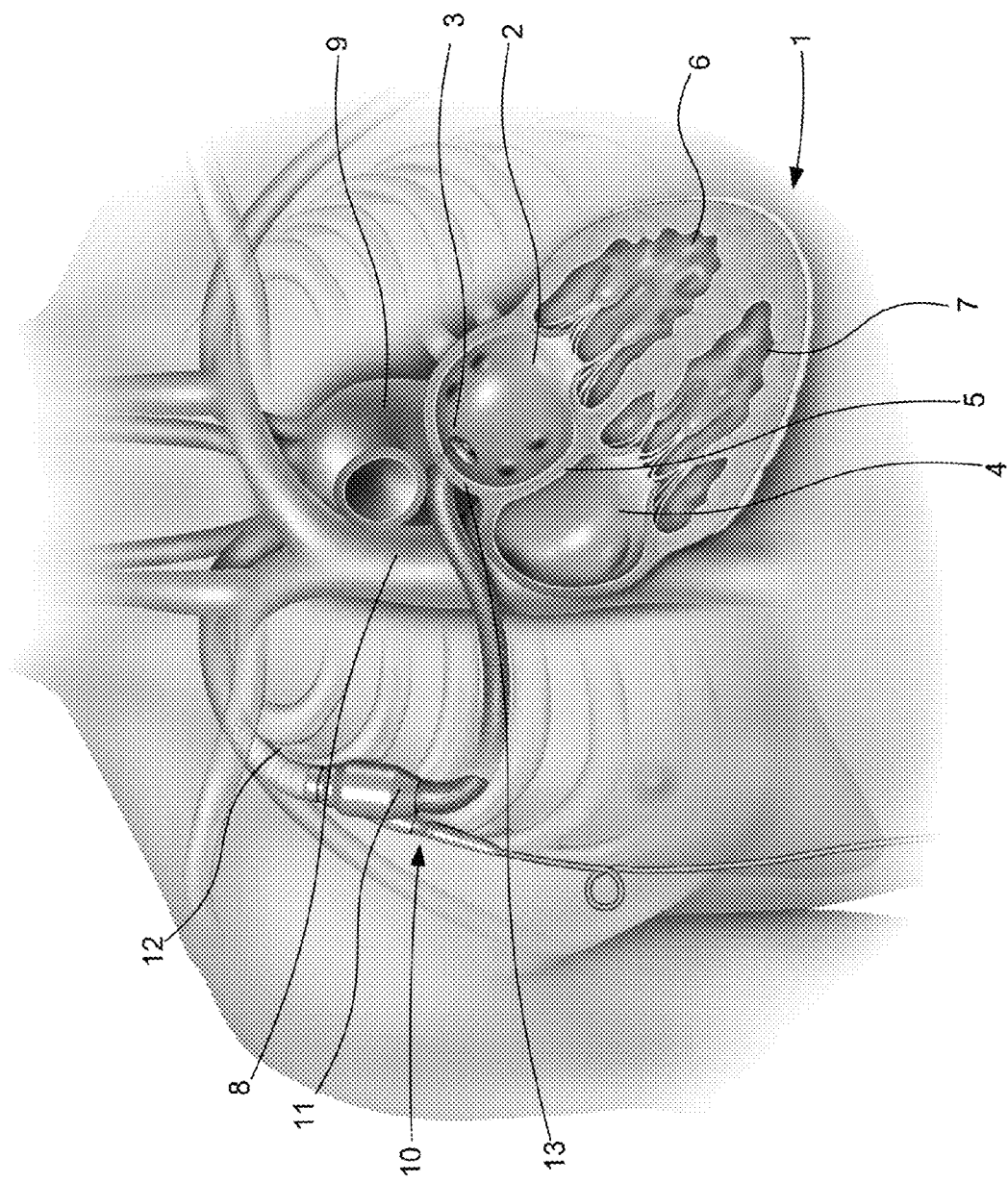
FIG. 1 is an illustration of a ventricular assist device (VAD) in place within a portion of a body of a patient according to an embodiment.

In some embodiments, a method includes coupling, at least temporarily, a support member adjacent to a target tissue. The support member is configured to support the target tissue and to define a path along which a cutting device can move. The method includes moving the cutting device along the path defined by the support member to cut and/or dilate the target tissue. In some embodiments, the method optionally includes disposing a cannula of a device within the cut defined in target tissue. The cannula is coupled to the target tissue such that a lumen defined by the cannula is in fluid communication with a volume defined at least in part by the target tissue.

In some embodiments, a method of coupling an inlet flow cannula of a ventricular assist device to a wall of an atrium of a heart includes moving at least one of the superior vena cava or the aorta to expose a portion of the wall of the atrium. A support member is at least temporarily coupled to the wall of the atrium such that movement of the wall in at least one direction is limited. A cutting device is moved along a path defined by the support member to cut the wall of the atrium. In some embodiments, the method optionally includes disposing the inlet flow cannula of the ventricular assist device within the cut defined in the atrium wall. The method includes coupling the inlet flow cannula to the wall of the atrium such that the inlet flow cannula is in fluid communication with the atrium.

In some embodiments, a method includes disposing a support member through an atrial wall when the support member is in a first (or expanded) configuration. The support member is moved from the first configuration to the second configuration such that a contact portion of the support member is non parallel to a guide portion of the support member. The contact portion is moved into contact with a first side of the atrial wall to limit movement of the atrial wall in at least one direction. A cutting device is moved along the guide of the support member to define an opening in the atrial wall from a second side of the atrial wall.

In some embodiments, the contact portion substantially surrounds the guide portion when the support member is in the second configuration. In some embodiments, the contact portion substantially surrounds the opening in the atrial wall.

In some embodiments, an apparatus includes a support member configured to limit movement of a target tissue (e.g., an atrial wall) during a surgical procedure. The support member has a distal end portion, a contact portion and a guide portion, and is configured to move between a first (expanded) configuration and a second (collapsed) configuration. The distal end portion is configured to pierce and or dilate the target tissue when the support member is in the first configuration. The contact portion is configured to contact the target tissue when the support member is in the second configuration to limit movement of the target tissue in at least one direction. The guide portion is configured to define a path along which a cutting tool can move to define an opening in the target tissue.

In some embodiments, the contact portion is configured to contact a first side of the target tissue when the support member is in the second configuration to limit movement of the target tissue in at least one direction. The guide portion is configured to define a path along which a cutting tool can move to define an opening in the target tissue from a second side of the target tissue.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to direction closer to and away from, respectively, an operator of a medical device. Thus, for example, the end of the device contacting the patient's body would be the distal end of the device, while the end opposite the distal end would be the proximal end of the device. Moreover, a portion of an anatomical structure can be considered as a reference to describe a position closer to or away from the portion of the anatomical structure. For example, an end of the superior vena cava that is closest to the heart would be the proximal end of the superior vena cava, while the end opposite the proximal end would be the distal end.

As used herein, the terms "about" and "approximately" generally mean plus or minus 10% of the value stated. For example, about 0.5 would include 0.45 and 0.55, about 10 would include 9 to 11, about 1000 would include 900 to 1100.

The term "substantially" when used in connection with "cylindrical," "linear," and/or other geometric relationships is intended to convey that the structure so defined is nominally cylindrical, linear or the like. As one example, a portion of a support member that is described as being "substantially linear" is intended to convey that, although linearity of the portion is desirable, some non-linearity can occur in a "substantially linear" portion. Such non-linearity can result from manufacturing tolerances, or other practical considerations (such as, for example, the pressure or force applied to the support member). Thus, a geometric construction modified by the term "substantially" includes such geometric properties within a tolerance of plus or minus 5% of the stated geometric construction. For example, a "substantially linear" portion is a portion that defines an axis or center line that is within plus or minus 5% of being linear.

As used herein, the term "stiffness" relates to an object's resistance to deflection, deformation, and/or displacement by an applied force. For example, a wire or support member with greater stiffness is more resistant to deflection, deformation and/or displacement when exposed to a force than a wire or support member having a lower stiffness. Similarly stated, a support member having a higher stiffness can be characterized as being more rigid than a support member having a lower stiffness. In some embodiments, the stiffness of an object can be characterized by the object's linear stiffness. Linear stiffness can be characterized in terms of the amount of force applied to the object and the resulting distance through which a first portion of the object deflects, deforms, and/or displaces with respect to a second portion of the object. When characterizing the linear stiffness of an object, the deflected distance may be measured as the deflection of a portion of the object different than the portion of the object to which the force is directly applied. Said another way, in some objects, the point of deflection is distinct from the point where force is applied.

Stiffness is an extensive property of the object being described, and thus is dependent upon the material from which the object is formed and certain physical characteristics of the object (e.g., shape and boundary conditions). For example, the stiffness of an object can be increased or decreased by selectively including in the object a material having a desired modulus of elasticity. The modulus of elasticity is an intensive property of the constituent material and describes an object's tendency to elastically (i.e., non-permanently) deform in response to an applied force. A material having a high modulus of elasticity will not deflect as much as a material having a low modulus of elasticity in the presence of an equally applied force. Thus, the stiffness of the object can be increased, for example, by introducing into the object and/or constructing the object of a material having a high modulus of elasticity. In another example, the stiffness of the object can be increased or decreased by changing the flexural modulus of a material of which the object is constructed. Flexural modulus is used to describe the ratio of the applied stress on an object in flexure to the corresponding strain in the outermost portions of the object. The flexural modulus, rather than the modulus of elasticity, is used to characterize certain materials, for example plastics, that do not have material properties that are substantially linear over a range of conditions. An object with a first flexural modulus is less elastic and has a greater strain on the outermost portions of the object than an object with a second flexural modulus lower than the first flexural modulus. Thus, the stiffness of an object can be increased by including in the object a material having a high flexural modulus.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. Thus, the stiffness of the object can be increased by increasing and/or changing the shape of the cross-sectional area of the object.

The embodiments and methods described herein can be used to facilitate the placement of a ventricular assist device system (referred to herein as a "VAD") that can be at least partially implanted into a portion of the body of a patient to assist the function of the heart. For example, FIG. 1 illustrates a VAD 10 that is in fluid communication with a heart 1. For reference and as shown in FIG. 1, the heart 1 includes and/or otherwise defines a left atrium 2, a right atrium 4, a left ventricle 6 and a right ventricle 7. The left atrium 2 and the right atrium 4 are separated by a septum 5. The left atrium 2 includes a wall 3 that defines a dome of the left atrium 2. The heart 1 is in fluid communication with the superior vena cava 8 (which provides blood flow into the right atrium 4) and the aorta 9 (which receives blood flow from the left ventricle 6). The heart 1 is described herein for reference and is not meant to be an exhaustive description of the heart 1. Therefore, the simplified discussion of the heart 1 is provided for context as it pertains to the embodiments described herein.

The VAD 10 includes a pump 11, an outlet flow cannula 12, and an inlet flow cannula 13. The pump 11 can include, for example, a high flow impeller pump and/or the like. In other embodiments, the pump 11 can be any suitable pump that is suitable for use in a VAD (e.g., any suitable pulsatile pump or continuous flow pump). The outlet flow cannula 12 can be, for example, a graft (e.g., a Dacron graft and/or any other suitable graft or graft material) that is physically and fluidically coupled to the pump outlet and also to the right subclavian artery or other suitable point in the circulatory system (e.g., via suturing or the like). The inlet flow cannula 13 is physically and fluidically coupled between the pump inlet and the left atrium 2. More specifically, as shown in FIG. 1, the inlet flow cannula is physically coupled to the wall 3 of the left atrium 2 that forms or otherwise defines at least a portion of the atrium dome. In this manner, oxygenated blood is drawn though the inlet flow cannula 13, into the pump 11, and through the outlet flow cannula 12, thereby aiding in the circulation of blood through the body.

The methods described herein include making an incision in the left atrial wall 3 (referred to herein as "atrial wall") through which the inlet flow cannula 13 (also referred to herein as "inflow cannula") can be inserted. Although the atrial wall is shown in FIG. 1 as being the dome of the left atrium, the methods and apparatus described herein can be suitable for any target tissue, such, for example, other regions of the atrium, and other portions of the anatomy unrelated to the heart. For example, in some embodiments, the methods and apparatus described herein can be used to incise the septum of the heart in, for example, a right atrial approach procedure.

Figure 2:
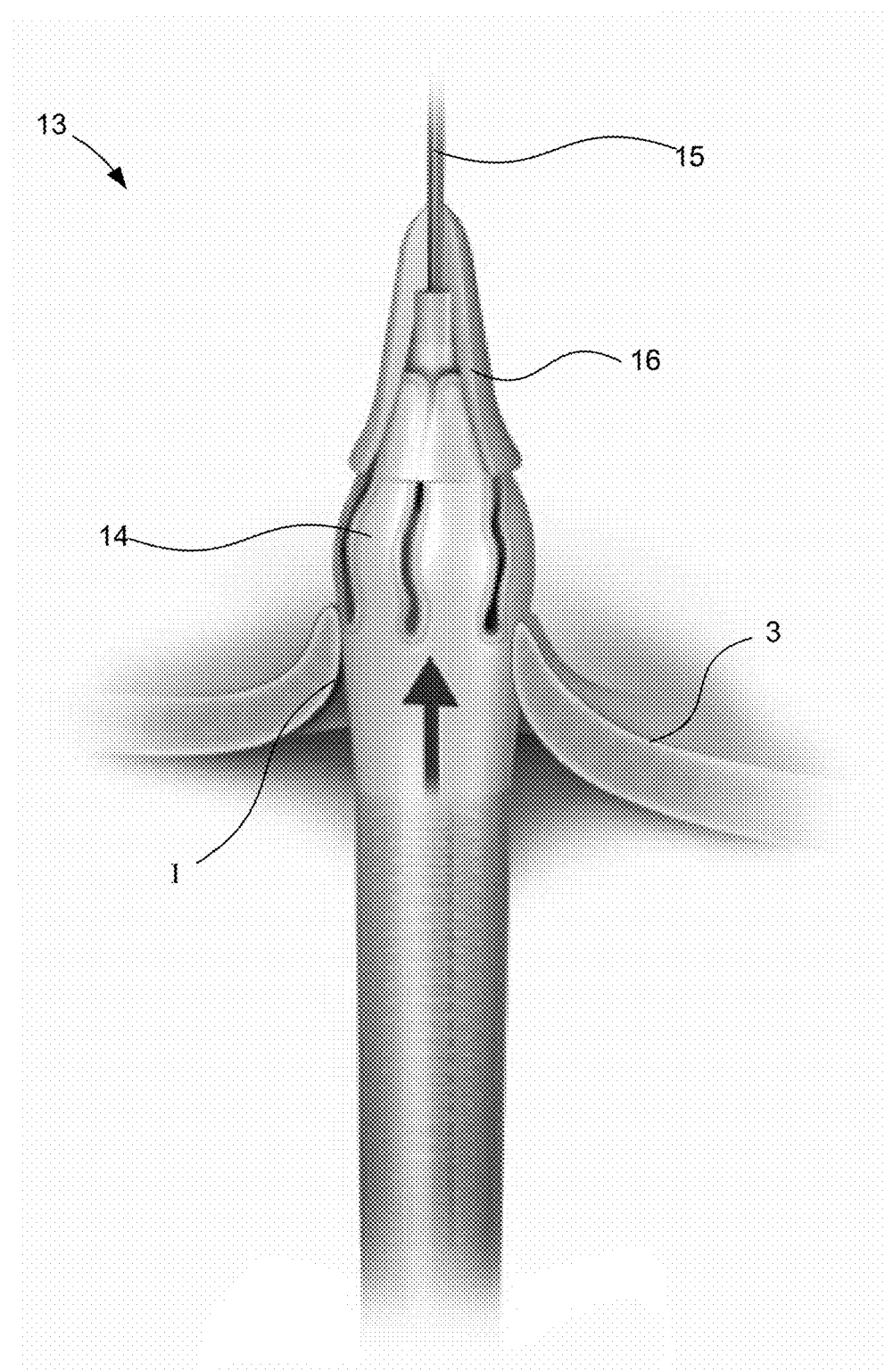
FIGS. 2-5 are illustrations of various stages of coupling an inlet flow cannula to a wall of an atrium of a heart according to an embodiment.
Figure 3:
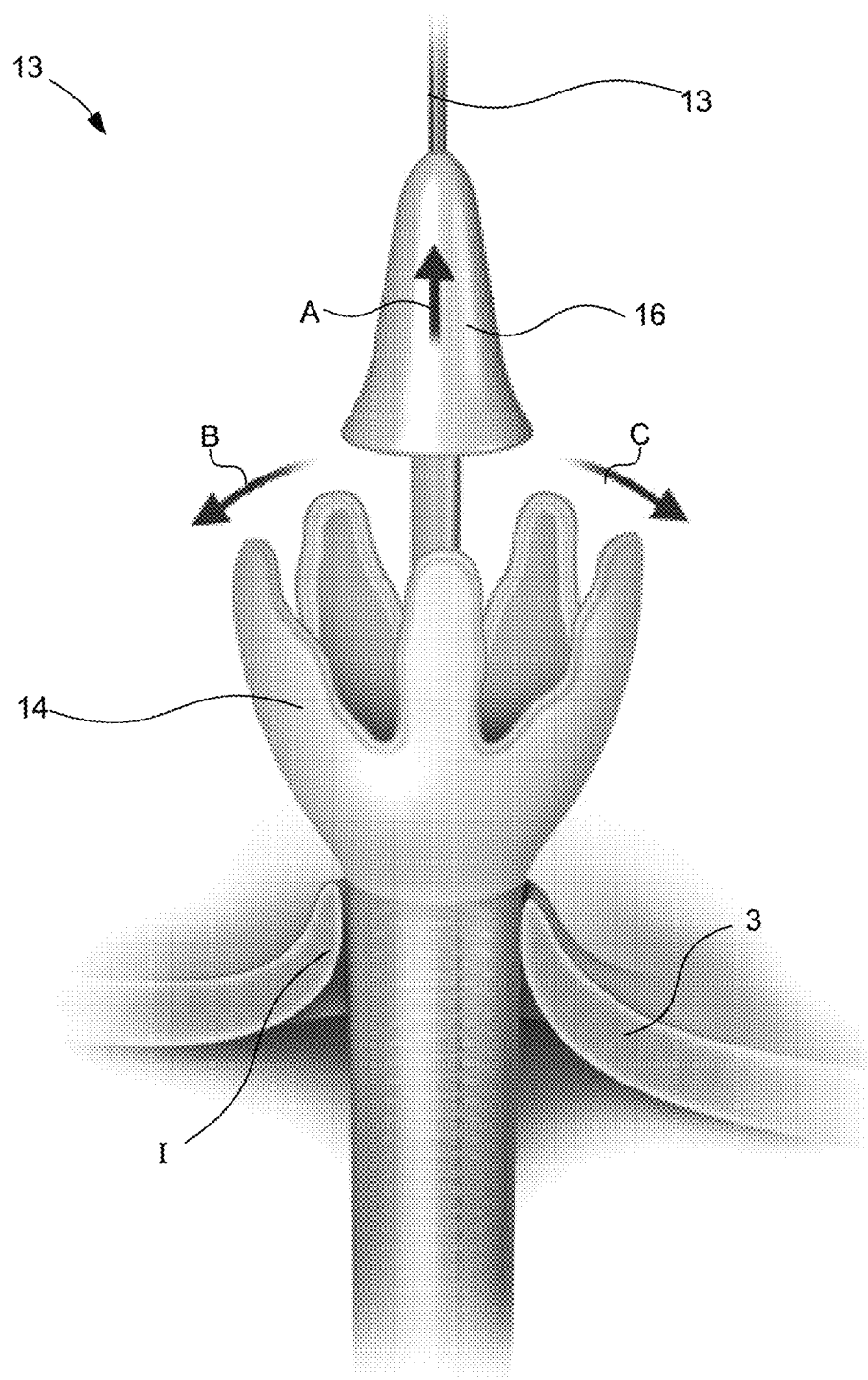
Figure 4:
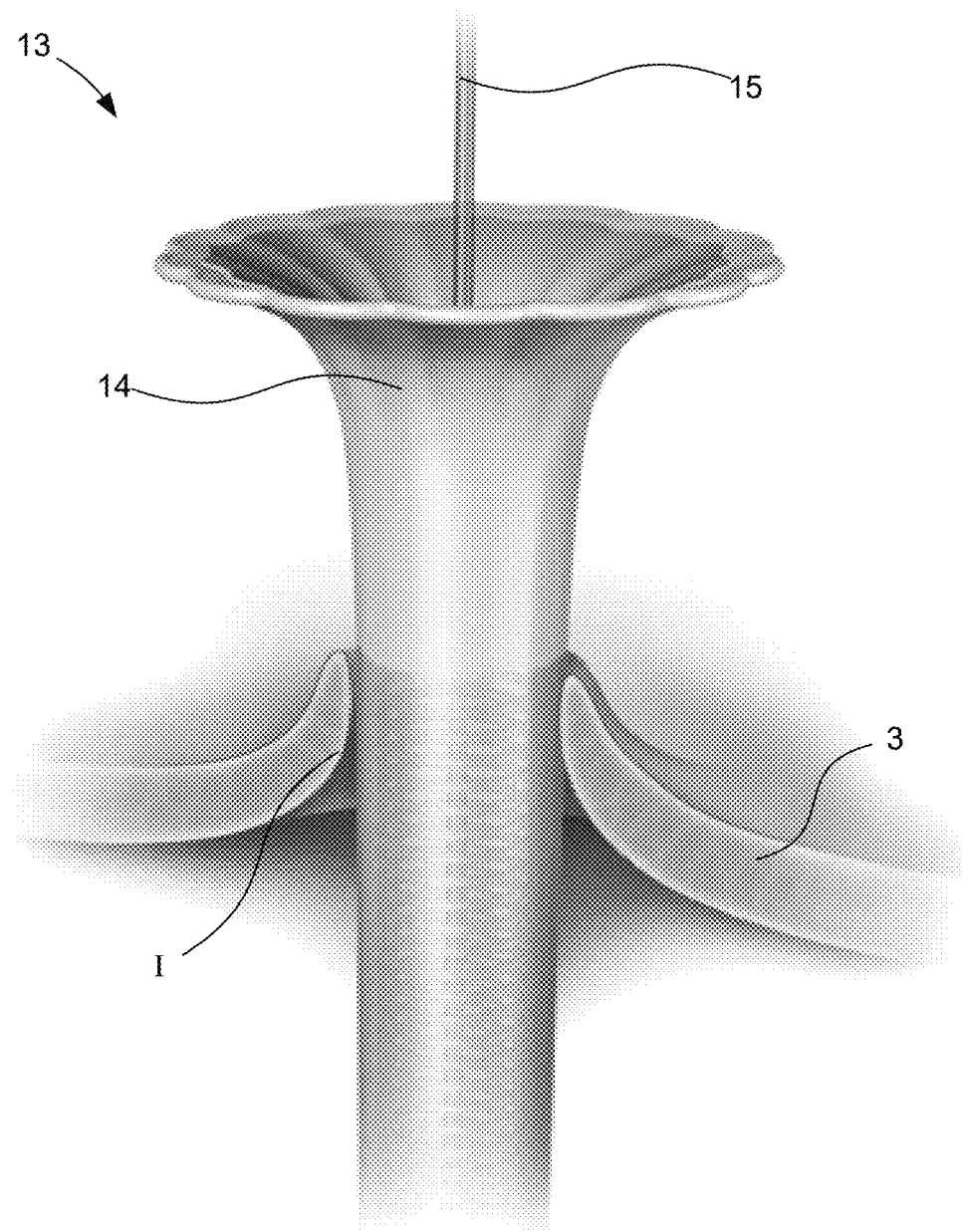
Figure 5:
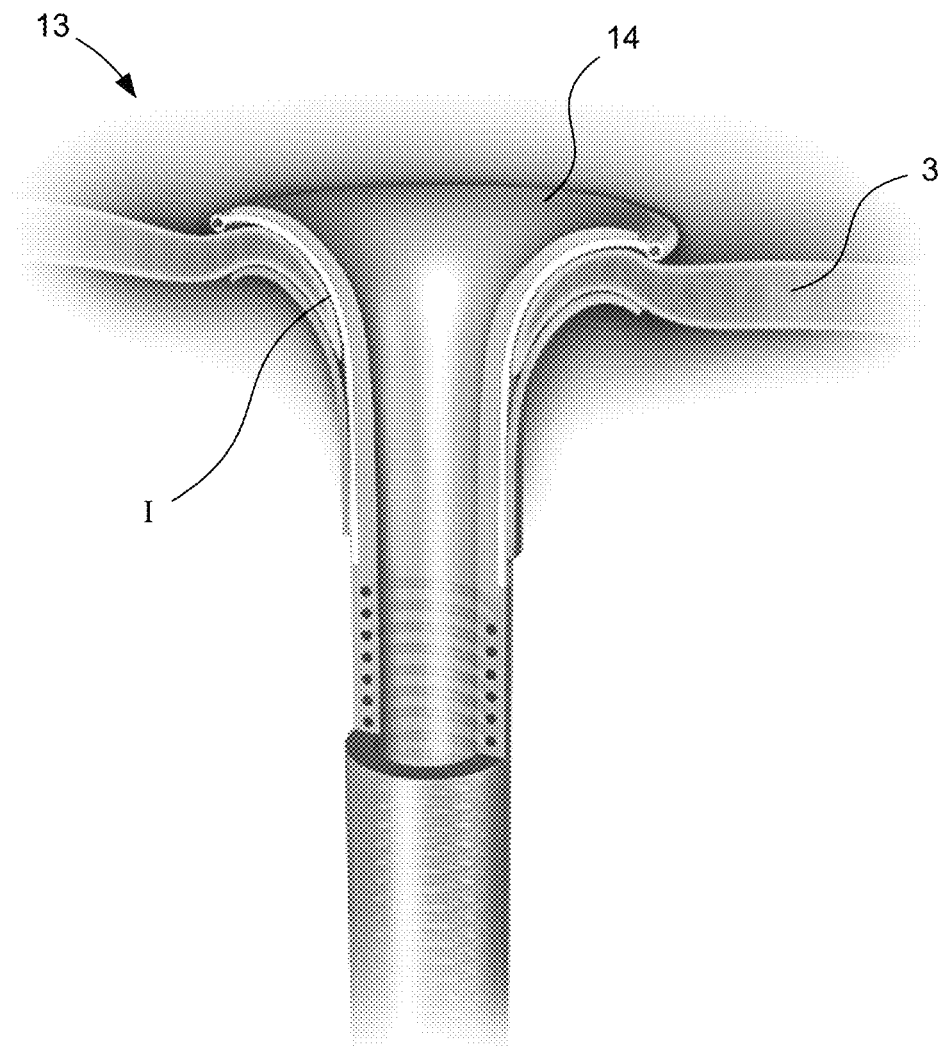

In some embodiments, the inflow cannula 13 can include a distal end portion that is suitable for coupling to the atrial wall 3. For example, FIGS. 2-5 illustrate the distal end portion 14 of the inflow cannula 13. The distal end portion 14 of the inflow cannula 13 can be transitioned between a first configuration in which the distal end portion 14 is collapsed and a second configuration in which the distal end portion 14 is expanded or open, for example, in a trumpet-shape or the like. As shown in FIGS. 2-5, the distal end portion 14 of the inflow cannula 13 can be moved along a guide wire 15 to be inserted into an incision I made in the atrial wall 3 of the heart 1. As shown in FIG. 2, the distal end portion 14 can be maintained in the first configuration by disposing at least a portion of the distal end portion 14 in a sheath 16 or other suitable structure. Once a desired part of the distal end portion 14 is inserted through the incision I in the atrial wall 3, the sheath 16 and/or the inflow cannula 13 can be moved relative to one another, thereby separating the sheath 16 from the distal end portion 14 of the inflow cannula 13, as indicated by the arrows A, B, and C in FIG. 3. In this manner, the distal end portion 14 of the inflow cannula 13 is allowed to unfold and/or otherwise transition to the expanded or open configuration, and can then be retracted to securely couple the distal end portion 14 of the inflow cannula 13 to the atrial wall 3 (e.g., the dome of the left atrium 2). Once coupled, the guide wire 15, the sheath 16 can be retracted from the inflow cannula 13 and removed from the body.

The anatomy of the heart 1, however, often makes forming the incision I in the atrial wall 3 difficult due at least in part to the limited thickness and susceptibility to tearing of the atrial wall 3. Moreover, the relatively low pressure within the left atrium 2 is such that when an inward force or pressure is applied (e.g., in the process of incising the atrial wall 3) the atrial dome can collapse. In some instances, forming the incision I while the atrial wall 3 is collapsed can result in an incision being too large (e.g., due at least in part on a change in diameter of the atrial wall 3). Thus, the embodiments described herein can be used to support, incise, and/or otherwise facilitate the coupling of an inflow cannula to a target tissue, such as, for example, the dome of the atrium.

Referring now to FIGS. 6-14, a support member 110 and a cutting device 120 are shown, according to an embodiment. The support member 110 can be any suitable device that can provide support to or backing for the atrial wall 3 to facilitate the incising of the atrial wall 3. For example, in some embodiments, the support member 110 can be shape memory device that can be transitioned between a first configuration (e.g., FIGS. 6-8) and a second configuration (e.g., FIG. 9). In some embodiments, the support member 110 can be formed from, for example, a nickel-titanium alloy or the like such as Nitinol™. In some embodiments, the support member 110 can be substantially cylindrical with a diameter between, for example, about 500 micrometers (μm) and about 3 millimeters (mm). In other embodiments, the support member 110 can have a diameter less than 500 μm. In still other embodiments, the support member 110 can have a diameter that is greater than 3 mm. The size of the diameter of the support member 110 can be such that the support member 110 is sufficiently stiff to pierce the atrial wall 3, as described in further detail herein. In some embodiments, the diameter of the support member 110 can vary along the length of the support member to facilitate piercing of the atrial wall 3. Said another way, in some embodiments a distal end portion of the support member 110 can be tapered. In some embodiments, a distal end portion of the support member 110 can form a cutting edge. The cutting edge can include, for example, a tapered tip, sharp point and/or series of serrations. In this manner, the support member 110 can be configured to pierce the atrial wall 3.

Figure 8:
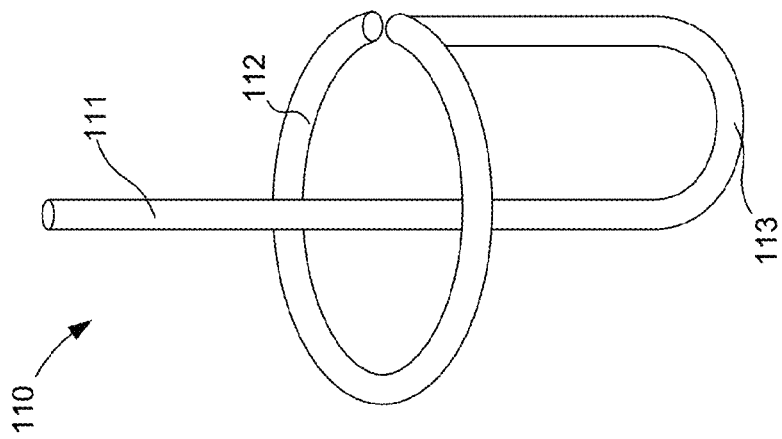
FIGS. 6-8 are a top view, a side view and a perspective view, respectively, of a support member in a first configuration, according to an embodiment.
Figure 7:
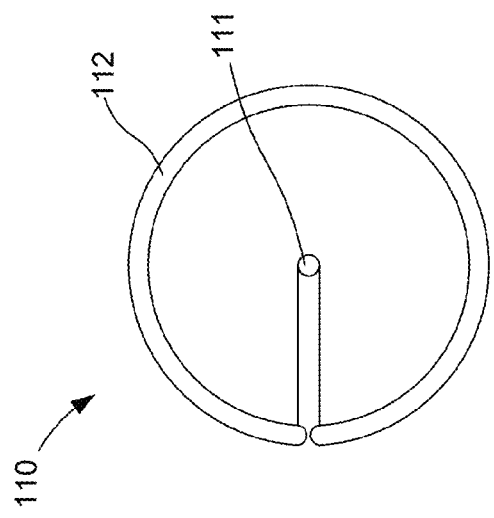
Figure 6:
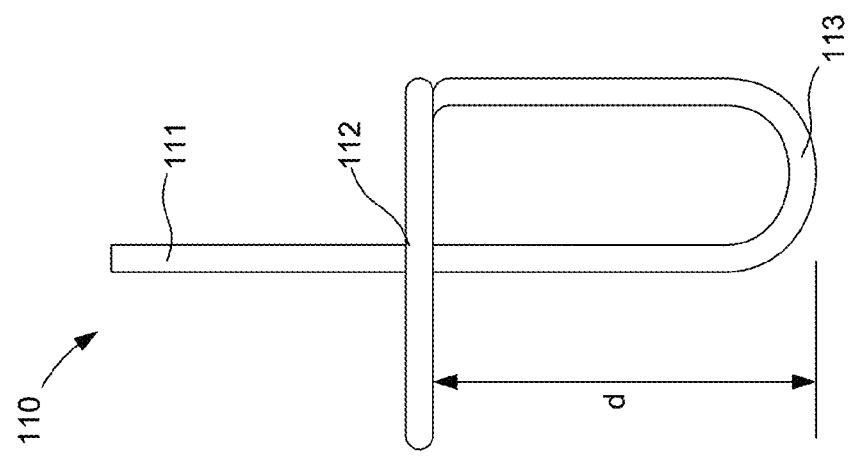

The support member 110 includes a proximal end portion 111, a distal end portion 112 and a central portion 113 therebetween. The proximal end portion 111 can be referred to as a guide portion, and the distal end portion 112 can include or be referred to as a contact portion. As shown in FIGS. 6-8, when in the first configuration, the distal end portion 112 of the support member 110 is non-linear. More specifically, as shown, when in the first configuration, the distal end portion 112 of the support member 110 forms a substantially annular ring that can be positioned inside the left atrium and pulled up (e.g., pulled outward or retracted) against the atrial wall 3 to provide a backing for and/or to otherwise support the atrial wall 3, as described in further detail herein. Similarly stated, when in the first configuration, the contact portion 112 of the support member 110 is configured to contact a surface of the atrium and substantially surround the proximal end portion 111. In this manner, the contact portion 112 can limit in at least one direction the movement of the atrial wall 3 when a cutting force or pressure is applied thereto. In some embodiments, when in the first configuration, the contact portion 112 can create a taut cutting and/or pressure site (also referred to herein as a "target portion") of the atrial wall 3. For example, the contact portion 112 can deform the atrial wall 3 (or any suitable organ wall) in a radial direction from the center point (i.e., away from where a puncture member or support member penetrates, punctures, or otherwise applies pressure to). In this manner, the atrial wall 3 can be moved into and/or held in a preferable position when a cutting force or pressure is applied thereto. In some instances, this can reduce the puncturing forces to penetrate the atrial wall 3. In some instances, the "stretching" of the atrial wall 3 can minimize and/or eliminate any "bunching" of the atrial wall 3 that may otherwise occur, and instead can produce a surface layer having a substantially constant thickness. In this manner, the contact portion 112 can cause movement of and/or stabilize at least a portion of the atrial wall 3 such that at least the portion of the atrial wall 3 is in a preferable position during the piercing and/or cutting.

As shown, for example, in FIGS. 6-9, the support member 110 has two ends and is continuous there between. Similarly, as shown, the support member 110 has a substantially constant diameter when the support member 110 is in the second configuration. Similarly stated, when the support member 110 is in the second configuration, the proximal end portion 111, the distal end portion 112, and the central portion 113 collectively define a substantially linear axis along the surface of the support member 110 and between the two ends of the support member 110. Such an arrangement allows for the support member 110 to have a relatively small profile or form factor. The small profile of the support member 110 when in the second configuration is particularly advantageous during insertion and removal of the support member 110. For example, the small profile can allow for a small incision or opening in the atrial wall 3 sufficient to receive the support member 110. The support member 110 can be formed in any suitable manner. In some embodiments, the support member 100 can be monolithically formed. Said another way, the guide portion 111, the contact portion 112 and the central portion 113 can all be monolithically formed.

The annular ring formed by the distal end portion 112 can be any suitable size. For example, in some embodiments, the distal end portion 112 can be configured to form an annular ring with a diameter that is between about 3 mm and about 13 mm. In other embodiments, the annular ring formed by the distal end portion 112 of the support member 110 can have a diameter that is less than 3 mm. In still other embodiments, the annular ring formed by the distal end portion 112 can have a diameter that is more the 13 mm.

Although shown in FIGS. 6-8 as forming a substantially annular ring, in other embodiments, the distal end portion 112 of the support member 110 can form any suitable shape. For example, in some embodiments, a distal end portion of a support member can form a substantially polygonal shape (e.g., square, rectangle, triangle, parallelogram, rhombus, etc.), a substantially rounded shape (e.g., oval, oblong, elliptical, etc.), and/or any suitable combination thereof. Moreover, the arrangement of the distal end portion 112 of the support member 110 can be such that when in the first configuration, the annular ring and/or the central portion 113 can have a stiffness sufficient to provide support to and/or backing for the atrial wall 3. In other words, the substantially annular ring and/or the central portion 113 can limit and/or reduce the movement, deflection and/or deformation of the atrial wall 3 in response to an applied force (e.g., resulting from a cutting device), as described in further detail herein.

In some embodiments, for example, the support member 110 can be constructed from a material having a modulus of elasticity between about 24 gigapascals (GPa) to about 83 GPa. In other embodiments, the shape of the distal end portion 112 and/or of the central portion 113 can be defined to increase the stiffness of the support member 110 when in the first configuration. For example, in some embodiments, the central portion 113 can have and/or can form a curved transition or the like between the proximal end portion 111 and the distal end portion 112 with a bend radius that can be related to a desired stiffness of at least the central portion 113. More specifically, in some embodiments, the bend radius of the central portion 113 can be relatively small, thereby increasing the stiffness of the central portion 113 compared to a resulting stiffness associated with a larger bend radius. Although the distal end portion 112 and the central portion 113 are shown in FIGS. 6 and 8 as forming a relatively smooth (e.g., continuous) bend radii, in other embodiments, the distal end portion 112 and/or the central portion 113 can include any number of bends, waves, ripples, etc., that can increase the stiffness of at least the distal end portion 112 and/or the central portion 113. In still other embodiments, the distal end portion 112 and/or the central portion 113 can be work hardened (e.g., hot worked and/or cold worked) and/or the like such that, when in the first configuration, a stress within the distal end portion 112 and/or the central portion 113 can, for example, resist deformation and/or deflection.

Additionally, the curved transition of the central portion 113 is positioned such that the linear portion of the support member 110 (i.e., a portion that is coaxial with and/or includes the proximal end portion 111) extends a distance 'd' beyond the contact portion 112 (see e.g., FIG. 6). This arrangement allows the proximal end portion 111 and/or the linear portion to define a path along which a cutting tool or other device can be moved. More particularly, because the guide path extends on either side of the annular ring defined by the contact portion 112, a cutting tool can be moved through the entire tissue wall and into a chamber (e.g., the atrium 3) defined by the tissue wall (e.g., the dome), as shown below in FIGS. 13 and 14. Said another way, a cutting tool can be moved about or along the guide path of the support member 110 from one side of the contact portion 112 (e.g., external to the tissue wall), to a second side of the contact portion 112 (e.g., inside the chamber). In this manner, the cutting tool can be moved beyond the contact portion 112 of the support member 110. Similarly stated, the contact portion 112 substantially surrounds (or circumscribes) the guide path defined by the support member 110. This allows the cutting tool to be moved along the guide path through the full cutting procedure, including the portion of the movement that occurs within the interior region of the organ.

Figure 9:
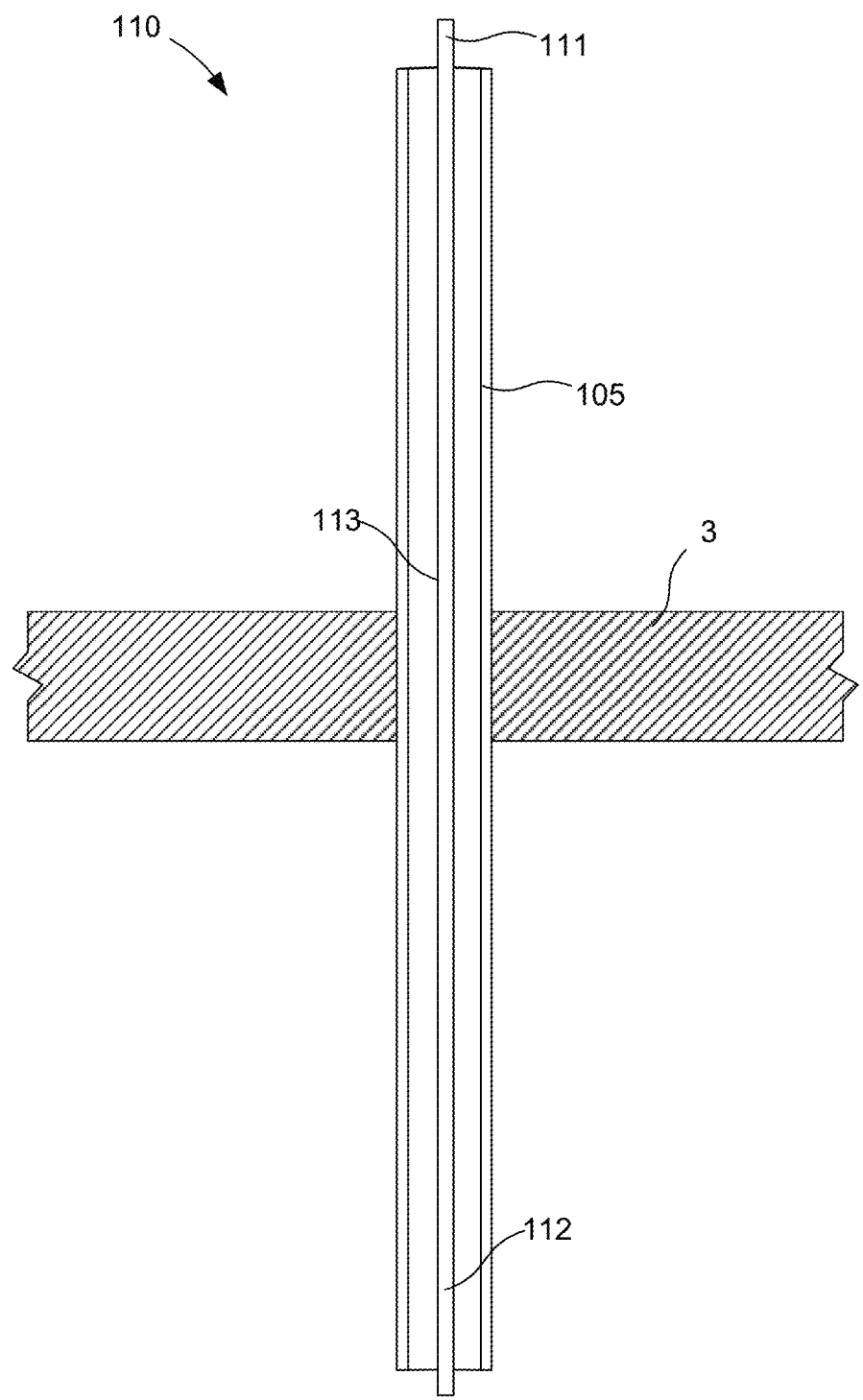
FIG. 9 is a cross-sectional side view of the support member of FIG. 6 in a second configuration.

As described above, the support member 110 can be transitioned between the first configuration and the second configuration. For example, in some instances, the support member 110 can be in the second configuration when disposed in an introducer catheter 105 or the like, as shown in FIG. 9. In such instances, the support member 110 can be in a substantially linear arrangement. Similarly stated, when in the second (or expanded) configuration, at least the distal end portion 112 of the support member 110 defines a center line that is substantially linear. In this manner, the support member 110 can be advanced through the introducer catheter 105 to a desired position relative to the atrial wall. In some embodiments, a doctor, surgeon, and/or the like can make a small incision in the atrial wall 3 and can insert at least a distal end portion of the introducer catheter 105 through the atrial wall 3, as shown in FIG. 9. In other instances, the introducer catheter 105 can be positioned such that an end surface is disposed adjacent to an outer surface of the atrial wall 3 and the support member 110 can be advanced through the introducer catheter 105, and can pierce the atrial wall 3 to be disposed within the left atrium (e.g., the left atrium 2 in FIG. 1). In other embodiments, a needle or the like can be used to insert a guidewire about which a dilator can be moved to dilate the atrial wall 3. In some instances, the introducer catheter 105 can be inserted into the dilated opening in the atrial wall 3.

As shown, for example, in FIGS. 10 and 11, the distal end portion 112 of the support member 110 can be advanced beyond the atrial wall 3 a sufficient distance to allow the support member 110 to transition from the second (or collapsed) configuration to the first (or expanded) configuration. For example, when disposed within the introducer catheter 105, the walls of the introducer catheter 105 can allow movement of the support member 110 in a substantially axial direction (e.g., proximal or distal direction) while substantially limiting movement of the support member 110 in any other direction. In this manner, the support member 110 can be maintained in the second configuration while disposed in the introducer catheter 105. When advanced beyond the introducer catheter 105 and into, for example, the left atrium, movement of the support member 110 is no longer limited and the distal end portion 112 can transition from the second (or linear) configuration to the first configuration, as shown in FIG. 10.

As shown in FIG. 11, with the distal end portion 112 of the support member 110 advanced beyond the atrial wall 3, the support member 110 can be retracted to an extent that places the annular ring formed by the distal end portion 112 in contact with an inner surface of the atrial wall 3. Thus, the distal end portion 112 of the support member 110 can be used as a "backer" for the cutting device 120 that can pierce the atrial wall 3 and pass through the annular ring formed by the distal end portion 112, as described in further detail herein. Similarly stated, in use, the contact portion 112 is placed into contact with the inner surface of the atrial wall 3 to maintain the position of and/or limit movement of the atrial wall during the cutting operation.

Figure 12:
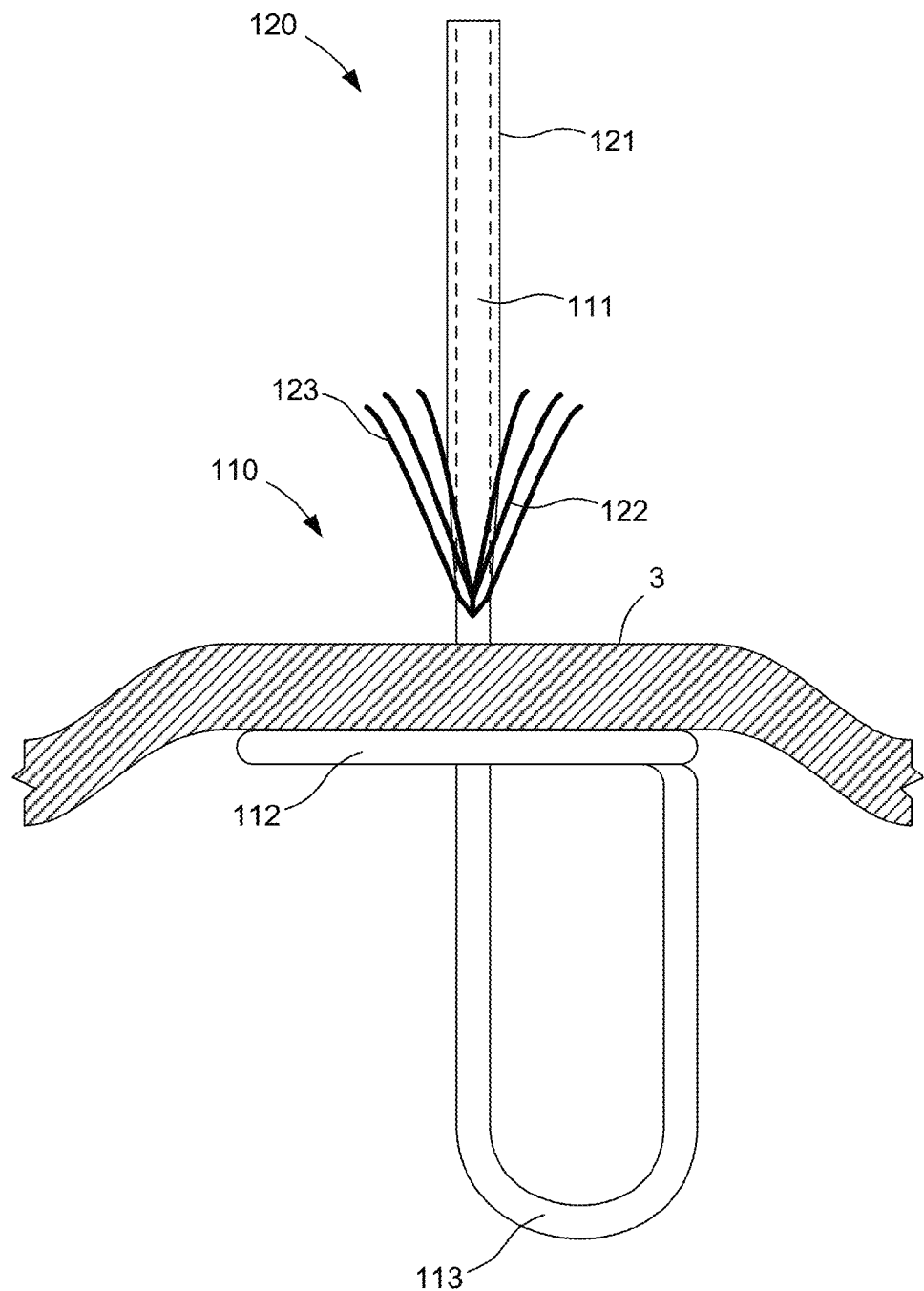
FIGS. 12-14 are side views of the support member of FIG. 6 and a cutting device in a first configuration, a second configuration, and a third configuration, respectively, according to an embodiment.
Figure 14:
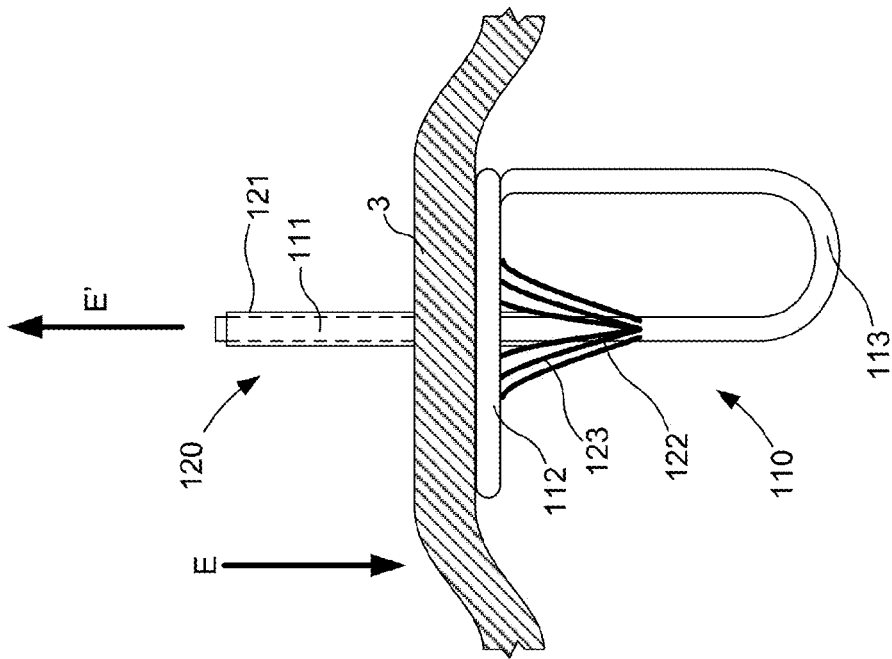
Figure 13:
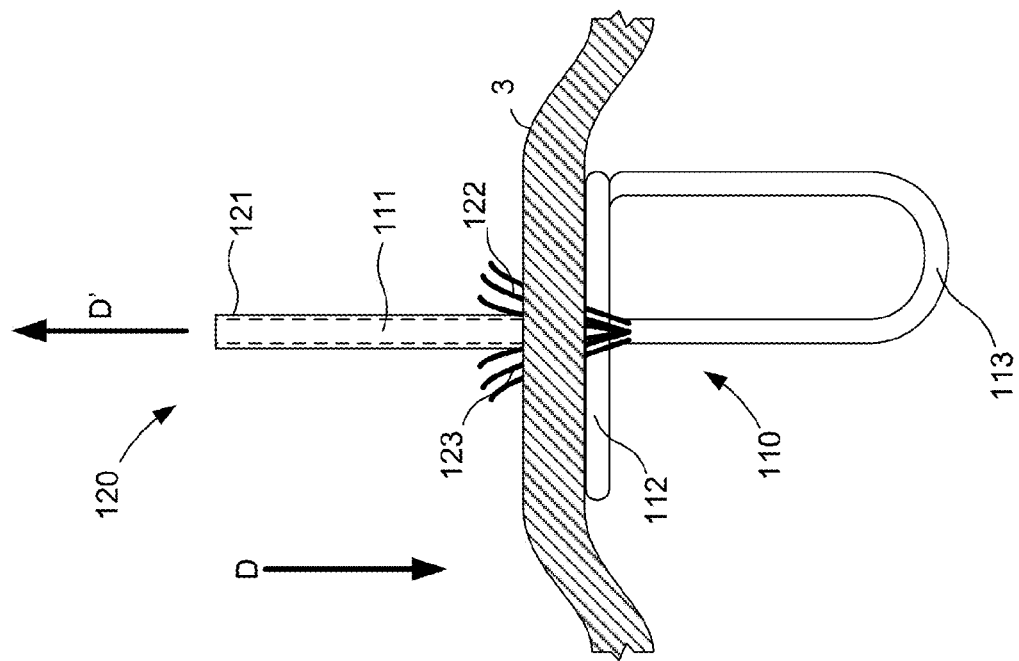

As shown in FIGS. 12-14, at least the proximal end (or guide) portion 111 of the support member 110 can define a path along which the cutting device 120 can move. More particularly, the proximal end portion 111 of the support member 110 can be substantially linear and can be configured to engage a portion of the cutting device 120, thereby acting as, for example, a guide wire or the like. The cutter device 120 can be any suitable device. For example, as shown in FIG. 12, the cutter device 120 includes a proximal end portion 121 and a distal end portion 122. The distal end portion 123 can include, for example, a set of blades, wires, sutures, strings, plugs, edges, and/or the like that can be configured to cut or incise a target tissue (e.g., the atrial wall 3). In some instances, the cutting device 122 can be slidably disposed about the proximal end portion 111 of the support member 110. In this manner, the cutting device 120 can be moved in the distal direction to place the blades 123 in contact with the atrial wall 3, as indicated by the arrow D in FIG. 13. The arrangement of the blades 123 of the cutting device 120 can be such that as the cutting device 120 is advanced relative to the atrial wall 3, the size of the incision is increased. In some instances, substantially the entirety of the blades 123 can be advanced through the atrial wall 3, as indicated by the arrow E in FIG. 14. Moreover, with the support member 110 in contact with an inner surface of the atrial wall 3, the support member 110 can exert a reaction force in response to an upward force exerted on the proximal end portion 111, as shown by arrows D' (FIG. 13) and E' (FIG. 14). In this manner, deformation of the atrial wall 3 can be minimized and the atrial wall 3 can be cut to define a desired incision that can receive, for example, a portion of an inlet flow cannula of a VAD (e.g., the inlet flow cannula 13 of the VAD 10 in FIG. 1), which can then be coupled the atrial wall 3 (e.g., via sutures, adhesives, and/or the like).

Although not shown in FIGS. 6-14, the distal end portion 122 of the cutting device 120 can be operably coupled to, for example, an actuator or the like that can be configured to retract and/or otherwise reduce the diameter of the distal end portion 122 of the cutting device 120. For example, in some embodiments, once the desired incision is defined in the atrial wall 3 (via the blades 123), the actuator can be actuated to reduce the diameter of, for example, at least a portion of the blades 123. In this manner, the blades 123 can be retracted through the atrial wall 3 and/or an introducer catheter (not shown in FIGS. 12-14) without undesirably cutting the atrial wall 3 and/or any other structure (e.g., anatomy and/or structure of the device).

Although described above as advancing substantially the entirety of the blades 123 of the cutting device 120 through the atrial wall 3, in other instances, the blades 123 can be partially advanced through the atrial wall 3 to an extent that is associated with a desired size of incision in the atrial wall 3. In such instances, the blades 123 can be moved in a distal direction relative to the atrial wall 3 until the incision is a desired size and, in some instances, an actuator or the like can be actuated to retract the blades 123. As a result, the cutting device 120 can be retracted through, for example, an introducer catheter or the like (not shown in FIGS. 12-14) and removed from the body. In some instances, the cutting device 120 can form an incision in the atrial wall 3 and a dilator or balloon can be inserted into the incision to dilate or otherwise increase a diameter of the incision.

Although the support member 110 is described above as transitioning from the second configuration to the first configuration in response to being advanced beyond an introducer catheter 105, in other embodiments, a support member can be configured to transition between the first configuration and the second configuration when any suitable transitioning criterion is satisfied. For example, in some embodiments, a support member can be configured to transition between the first configuration and the second configuration (or vice versa) in response to a current, tension force, compression force, and/or the like. In some embodiments, the support member 110 can be constructed from a shape memory material that can transition between a first configuration and a second configuration in response to an applied heat. For example, in some embodiments, the support member 110 can be constructed from a material that can have a transition temperature below that of the nominal bodily temperature (i.e., about 98 degrees Fahrenheit (° F.)). Thus, when the support member 110 is maintained at or below the transition temperature (e.g., maintained at or below, for example, 85° F.), the support member 110 is maintained in the second configuration. When, after a sufficient period of time, the support member 110 is heated above the transition temperature (e.g., as a result of being disposed in the body), the support member 110 can then transition to the first (or collapsed) configuration (see e.g., FIGS. 6-8). In some embodiments, a support member can be configured to transition between a series of configuration (e.g., more than two configurations). For example, in the embodiments where the support member 110 is formed from a shape memory material that transitions in response to an applied heat, the support member 110 can transition between any number of configurations to control the rate of transition and/or the like. In this manner, potential damage to bodily tissue as a result of the support member 110 rapidly transitioning from the first configuration to the second configuration can be reduced and/or eliminated.

Figure 15:
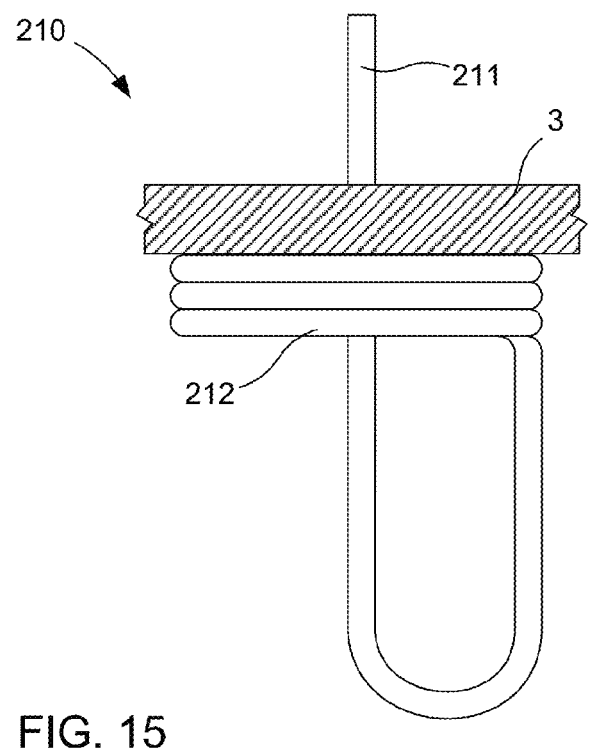
FIG. 15 is a side view of a support member according to another embodiment.

While the support device 110 is shown and described above as forming a single annular ring, in other embodiments, a support device can be configured to form any number of annular rings or structures configured to contact or be disposed adjacent to the target tissue. For example, FIG. 15 is a schematic illustration of a support device 210 according to another embodiment. The support device 210 includes a proximal end portion 211 and a distal end portion 212 that can be placed in contact with, for example, the atrial wall 3 of the heart 1 (see e.g., FIG. 1). The support device 210 can be substantially similar in form and function to the support device 110; therefore, aspects of the support device 210 are not described in further detail herein. The support device 210 can differ from the support device 110, however, in that the distal end portion 212 forms multiple annular rings or coils when in the collapsed configuration. The set of annular rings can have a stiffness that is substantially greater than a stiffness of a single annular ring. In this manner, when in the first configuration and when in contact with a surface of the atrial wall 3 (see e.g., FIG. 15), the distal end portion 212 of the support member 210 can have a stiffness that is sufficient to support the atrial wall 3 such that a small amount of deflection and/or deformation of the atrial wall 3 occurs under a given amount of force.

Figure 16:
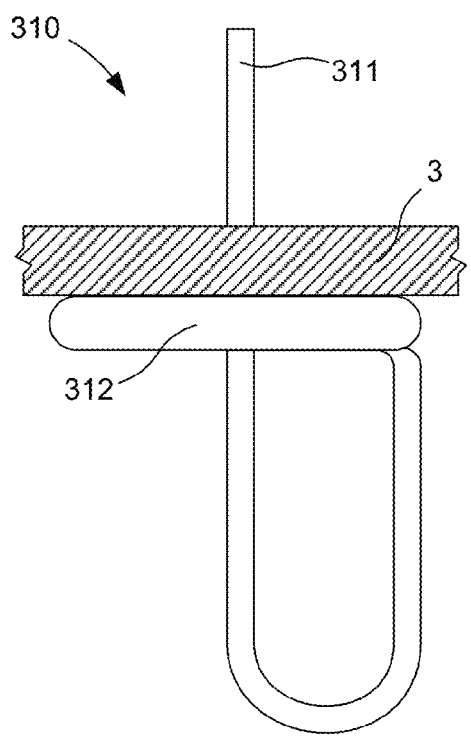
FIG. 16 is a side view of a support member according to another embodiment.

In some embodiments, the stiffness of an annular ring formed by a distal end portion of a support member can be increased by changing (e.g., increasing) the diameter of at least part of the distal end portion. For example, FIG. 16 is a schematic illustration of a support device 310 according to another embodiment. The support device 310 includes a proximal end portion 311 and a distal end portion 312 that can be placed in contact with, for example, the atrial wall 3 of the heart 1. As shown in FIG. 16, the distal end portion 312 of the support member 310 has a diameter that is larger than a diameter of the proximal end portion 311. In this manner, the distal end portion 312 of the support member 310 can have a greater stiffness without increasing the overall length of the support member 310 to form additional annular rings and/or without increasing the diameter of the entire support member 310. When in the first configuration and when placed in contact with a surface of the atrial wall, the annular ring formed by the distal end portion 312 of the support member 310 can support and/or otherwise back the atrial wall 3 to limit and/or reduce deflection and/or deformation when a cutting device (e.g., the cutting device 120) is advanced through the atrial wall 3.

Although the support members 110, 210, and 310 are shown and described as being inserted into the atrium and placed in contact with an inner surface to support the atrial wall, in other embodiments, a support member can include a first portion that is placed in contact with an inner surface of the atrium and a second portion that is placed in contact with an outer surface of the atrium. For example, a support member can include a distal end portion that is configured to form a first annular ring that is disposed within the atrium and in contact with an inner surface, and a second annular ring that is disposed outside of the atrium and in contact with an outer surface. In this manner, the atrial wall can be supported by the support member on the inner surface and the outer surface which can, in some instances, further limit deformation of the atrial wall and/or limit the extent of an incision formed in the atrial wall (i.e., to prevent the incision from becoming too large).

Although the support members 110, 210, and 310 are shown in FIGS. 6-16 as transitioning between a first configuration and a second configuration to form a contact portion that can be placed in contact with the atrial wall of the heart to support the wall during an atrial wall cutting procedure, in other embodiments, a support member can be configured to support the atrial wall without transitioning between a first configuration and a second configuration. Moreover, although the support member 110, 210, and 310 are shown as contacting an inner (or first) side of the atrial wall to support an incision produced from an outer (or second) side of the atrial wall, in other embodiments, the supporting and the cutting can both occur from a single side. For example, FIGS. 17-20 illustrate a support member 410 according to another embodiment. The support member 410 has a proximal end portion 411 and a distal end portion 412. The support member 410 includes an outer catheter 414 and an inner catheter 415 and defines an inner volume 416 therebetween. More particularly, the inner catheter 415 can be disposed within a lumen defined by the outer catheter 414. The outer catheter 414 can have an inner diameter that is larger than an outer diameter of the inner catheter 414. Thus, the inner volume 416 is defined between an inner surface of the outer catheter 414 and an outer surface of the inner catheter 415. The inner catheter 415 defines a lumen 417 that is configured to receive a cutting device 420 (see e.g., FIGS. 18-20).

Figure 17:
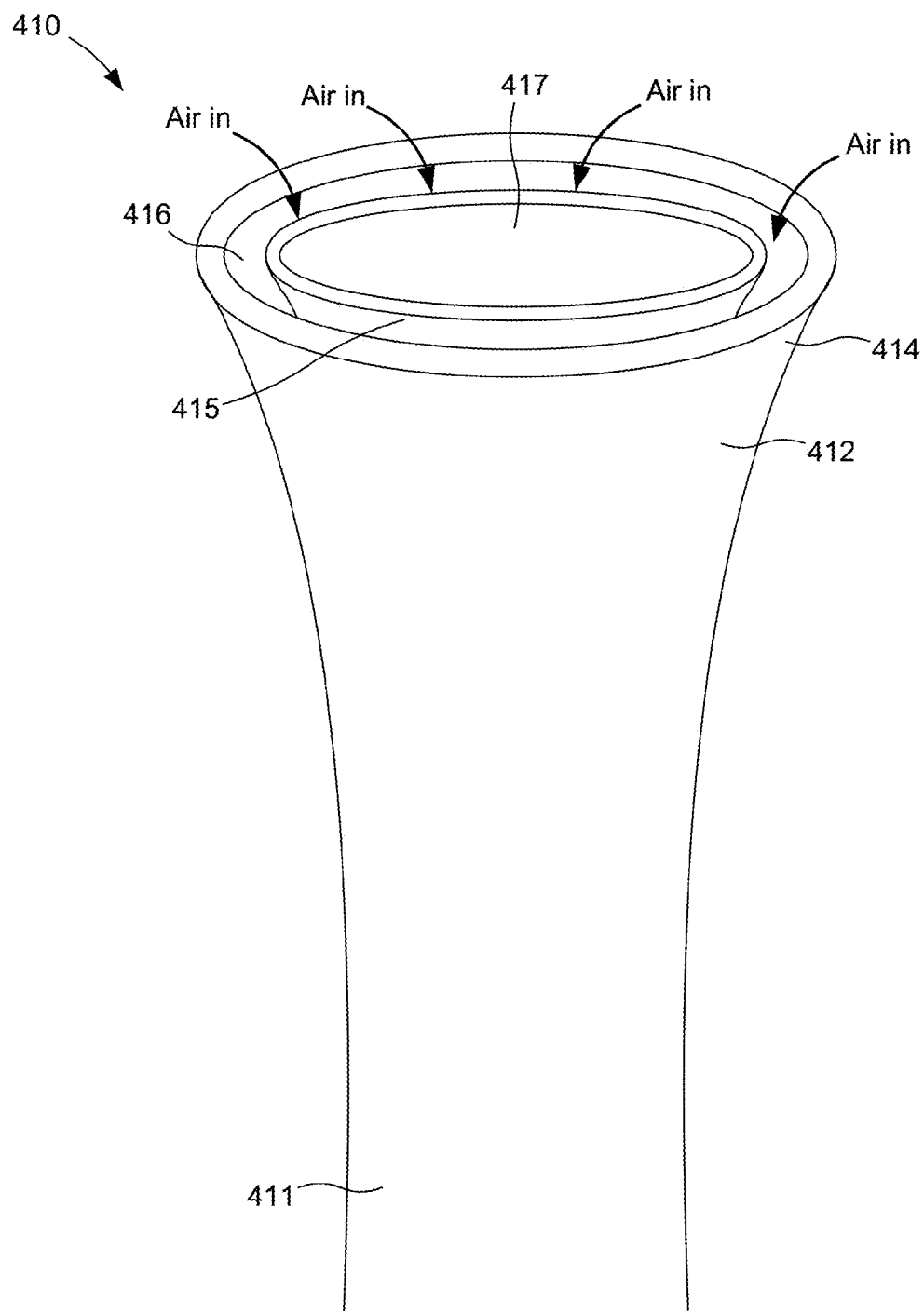
FIG. 17 is a perspective side view of a support member according to another embodiment.

As shown in FIG. 17, the distal end portion 412 of the support member 410 is tapered and/or flared. Similarly stated, the support member 410 can have an outer diameter that increases along a length of the support member 410 from a first diameter at the proximal end portion 411 to a second diameter, larger than the first diameter, at the distal end portion 412 of the support member 410. Thus, when the distal end portion 412 of the support member 410 is placed in contact with a bodily tissue, the surface area of the bodily tissue in contact with the distal end portion 412 is increased compared to the surface area that would result with a substantially constant outer diameter. In some instances, the increase in the surface area can, for example, minimize a risk of tearing the bodily tissue in contact with the distal end portion 412. Although the outer catheter 414 and the inner catheter 415 are shown in FIG. 17 as being flared, in other embodiments, the support member 410 can include an inner catheter that has a substantially constant diameter and an outer catheter that is flared at the distal end portion.

The proximal end portion 411 of the support member 410 is configured to be operably coupled to a vacuum source such that the vacuum source is placed in fluid communication with the inner volume 416 defined between the outer catheter 414 and the inner catheter 414. The arrangement of the support member 410 and the vacuum source can be such that when the vacuum source is actuated (e.g., turned on to exert a vacuum and/or suction force), a negative pressure is produced in the inner volume 416 that draws air or fluid into the inner volume 416, as shown in FIG. 17. In this manner, the support member 410 can be configured to operably cooperate with the vacuum source and/or suction force to apply tension to the atrial wall 3. Similarly stated, the support member 410 (e.g., the distal end portion 412) and the vacuum source can operably function to limit movement in at least one direction of a target portion of the atrial wall 3 during a cutting procedure.

More specifically, the distal end portion 412 and the suction force collectively can create a taut cutting and/or pressure site (also referred to herein as a "target portion") of the atrial wall 3. For example, the distal end portion 412 can deform the atrial wall 3 (or any suitable organ wall) in a radial direction from the center point (i.e., away from where a puncture member or support member penetrates, punctures, or otherwise applies pressure to). In this manner, the atrial wall 3 can be moved into and/or held in a preferable position when a cutting force or pressure is applied thereto. In some instances, this can reduce the puncturing forces to penetrate the atrial wall 3. In some instances, the "stretching" of the atrial wall 3 can minimize and/or eliminate any "bunching" of the atrial wall 3 that may otherwise occur, and instead can produce a surface layer having a substantially constant thickness. In this manner, the distal end portion 412 can cause movement of and/or stabilize at least a portion of the atrial wall 3 such that at least the portion of the atrial wall 3 is in a preferable position during the piercing and/or cutting.

Figure 18:
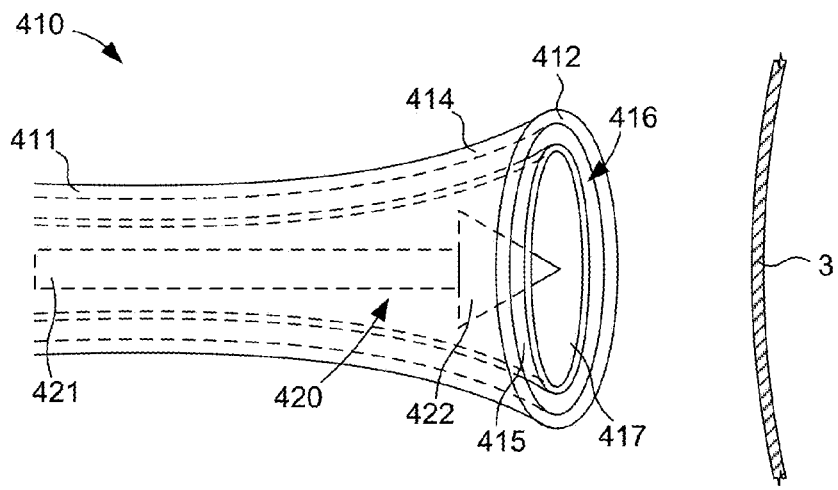
FIGS. 18-20 are schematic illustrations of the support member of FIG. 17 and a cutting device in a first configuration, a second configuration, and a third configuration, respectively, according to an embodiment.
Figure 19:
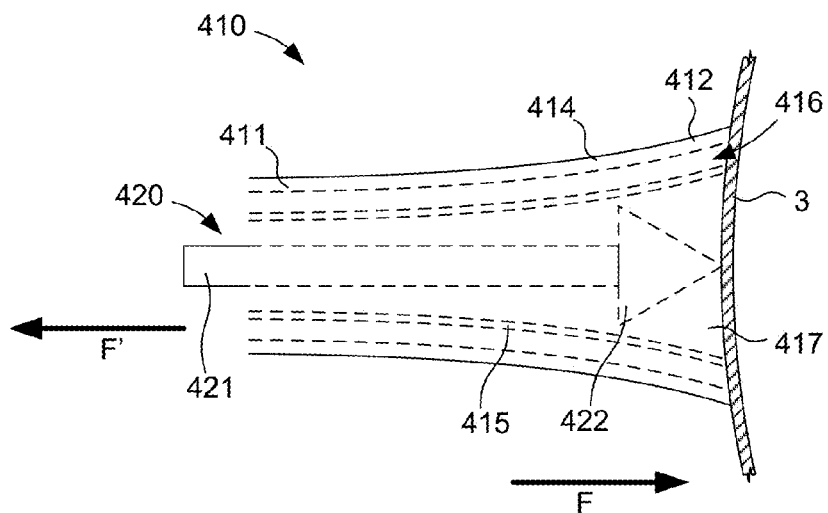
Figure 20:
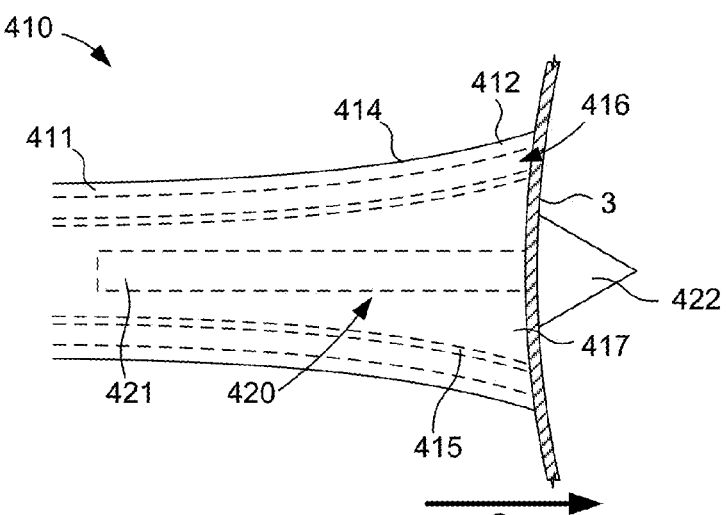

As shown in FIGS. 18-20, the support member 410 can be placed in contact with the atrial wall 3 to support the atrial wall 3 during a cutting procedure. For example, as shown in FIGS. 18 and 19, the support member 410 can be moved in a distal direction to place a distal surface of the support member 410 in contact with a surface of the atrial wall 3, as indicated by the arrow F in FIG. 19. Once in contact with the atrial wall 3, the vacuum source (not shown in FIGS. 17-20) can be actuated to produce a negative pressure in the inner volume 416, as described above. The negative pressure can exert a suction force on the atrial wall 3 that is sufficient to couple, at least temporarily, the support member 410 to the atrial wall 3. Moreover, the suction force can be sufficient to maintain the coupling between the support member 410 and the atrial wall 3 when a suitable external force is exerted upon the support member 410 and/or the atrial wall 3. For example, in some instances, it may be desirable to gently pull on the support member 410, as shown by the arrow F', to increase an amount of tension in the atrial wall 3. The increase in tension in the atrial wall 3 can aid in resisting deformation of the atrial wall 3 during a cutting event.

As shown in FIG. 20, when the desired amount of suction is applied to the atrial wall 3 and the desired amount of tension is applied to the atrial wall 3, the cutting device 420 can be moved in the distal direction relative to the support member 410 to pierce and/or cut the atrial wall 3. More specifically, as shown in FIGS. 18-20, the cutting device includes a proximal end portion 421 and a distal end portion 422. The proximal end portion 421 of the cutting device 420 can be manipulated by a user (e.g., a doctor, surgeon, physician, technician, etc.) to move the cutting device 420 relative to the support member 410. The distal end portion 422 of the cutting device 420 can be any suitable cutting member. For example, in some embodiments, the distal end portion 422 of the cutting device 420 can be substantially similar to the distal end portion 122 of the cutting device 120 (FIGS. 12-14). Thus, the cutting device 420 can be moved in the distal direction to cut the atrial wall 3, as indicated by the arrow G in FIG. 20. The coupling of the support member 410 to the atrial wall 3 can be such that as the distal end portion 422 of the cutting device 420 is advanced in the distal direction, the deflection of the atrial wall 3 prior to the distal end portion 422 of the cutting device 420 cutting the atrial wall 3 is minimized. Similarly stated, the support member 410 can maintain the position of the atrial wall 3 during the cutting operation. Thus, the cutting device 420 can produce a substantially clean cut without undo tearing of the atrial wall 3, which can be exacerbated by movement of the atrial wall 3. Once the cutting device 420 cuts the atrial wall 3, the vacuum source can be switched to an "off" position and the negative pressure maintain the coupling between support member 410 and the atrial wall 3 is removed. Thus, the support member 410 can be retracted from the atrial wall 3.

Although the support member 410 is particularly shown in FIGS. 17-20, in other embodiments, a support member that is configured to couple to the atrial wall of the heart via a suction force can be in any suitable arrangement and/or configuration. For example, FIGS. 21 and 22 are illustrations of a support member 510 according to another embodiment that can be used to apply a contact force to the atrial wall from a side entry. The support member 510 has a proximal end portion 511 and a distal end portion 512. As shown in FIG. 21, the support member 510 includes an outer ring 514 and an inner ring 515 and defines an inner volume 516 therebetween. The inner ring 515 defines a lumen 517 that can receive a cutting device (not shown in FIGS. 21 and 22). The proximal end portion 511 of the support member 510 is substantially closed (FIG. 22). The distal end portion 512 of the support member 510 is open (FIG. 21). The support member 510 also includes a suction tube 518 that is in fluid communication with the inner volume 516. A proximal end portion of the suction tube (not shown in FIGS. 21 and 22) can be operably coupled to a vacuum source. In this manner, the support member 510 can function to apply a suction force to a target tissue (or target portion) substantially similar to or the same as the support member 410 of FIGS. 17-20.

For example, the support member 510 can be configured to operably cooperate with the vacuum source and/or suction force to apply tension to the atrial wall 3. Similarly stated, the support member 510 (e.g., the distal end portion 512) and the vacuum source can operably function to limit movement in at least one direction of a target portion of the atrial wall 3 during a cutting procedure.

More specifically, the distal end portion 512 and the suction force collectively can create a taut cutting and/or pressure site (also referred to herein as a "target portion") of the atrial wall 3. For example, the distal end portion 512 can deform the atrial wall 3 (or any suitable organ wall) in a radial direction from the center point (i.e., away from where a puncture member or support member penetrates, punctures, or otherwise applies pressure to). In this manner, the atrial wall 3 can be moved into and/or held in a preferable position when a cutting force or pressure is applied thereto. In some instances, this can reduce the puncturing forces to penetrate the atrial wall 3. In some instances, the "stretching" of the atrial wall 3 can minimize and/or eliminate any "bunching" of the atrial wall 3 that may otherwise occur, and instead can produce a surface layer having a substantially constant thickness. In this manner, the distal end portion 512 can cause movement of and/or stabilize at least a portion of the atrial wall 3 such that at least the portion of the atrial wall 3 is in a preferable position during the piercing and/or cutting.

Figure 23:
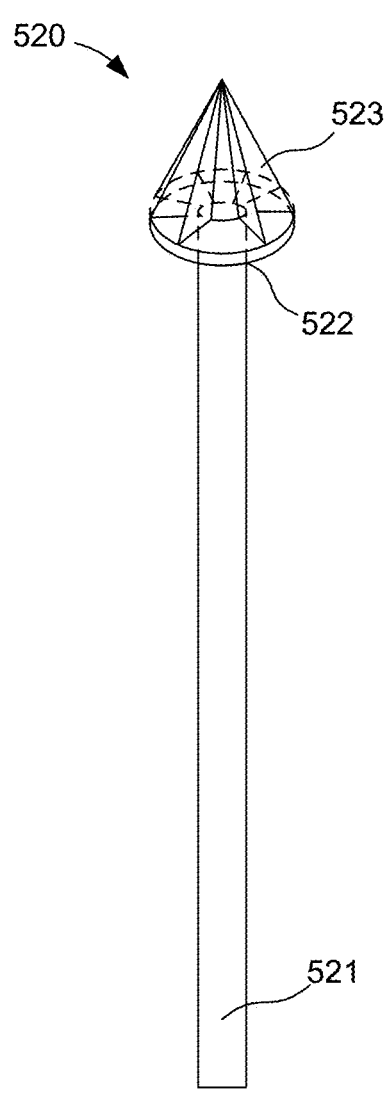
FIG. 23 is a schematic illustration of a cutting device according to an embodiment.

Any of the support members, 110, 210, 310, 410, and/or 510 can be used in conjunction with any suitable cutting device described herein. For example, FIG. 23 is a schematic illustration of a cutting device 520 according to an embodiment. The cutting device 520 has a proximal end portion 521 and a distal end portion 522. In some embodiments, the support member 520 can be movably disposed about a support member. In other embodiments, the support member 520 can be movably disposed within a lumen defined by a support member. Although not shown in FIG. 23, the proximal end portion 521 of the cutting device 520 can be any suitable shape, size, or configuration. For example, in some embodiments, the proximal end portion 521 of the cutting device 520 can include a user interface device such as a handle or the like. In this manner, a user (e.g., a doctor, surgeon, physician, technician, etc.) can manipulate the proximal end portion to, for example, move the cutting device relative to an atrial wall, as described in detail above.

Figure 24:
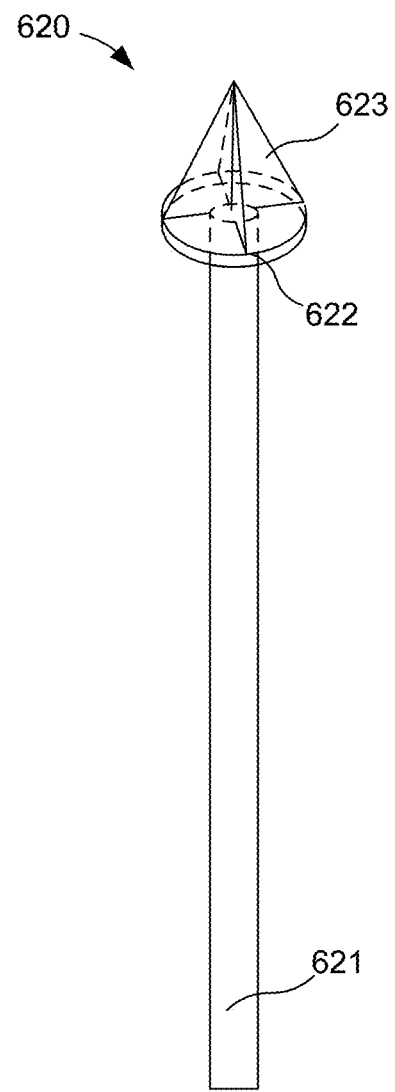
FIG. 24 is a schematic illustration of a cutting device according to another embodiment.

The distal end portion 522 of the cutting device 520 includes and/or defines a set of cutting members 523. In some embodiments, a distal end portion of each cutting member 523 can be coupled together to form a cutting edge. In some embodiments, the cutting members 523 can be made from, for example, a series of wires that converge to a sharp point. Any suitable number of wires can be used to form the cutting members 523. For example, as shown in FIG. 23, the distal end portion 522 of the cutting device 520 can include eight cutting members 523. In other embodiments, the distal end portion 522 can include more than eight cutting members 523. In other embodiments, the distal end portion 522 can include less than eight cutting members 523. For example, FIG. 24 is an illustration of the cutting device 620 according to another embodiment. The cutting device 620 includes a proximal end portion 621 that is substantially similar to the proximal end portion 521 of the cutting device 520. The distal end portion 622 of the cutting device 620 includes and/or defines a set of four cutting members 623.

Although the cutting members 523 and 623 of the cutting devices 520 and 620, respectively, are described as including wires that form the cutting members 523 and 623, respectively, in other embodiments, a cutting device can include cutting members that are, for example, blades or the like. In some embodiments, the cutting members 523 and 623 can be substantially similar in shape and size and can be disposed at substantially equal spacing circumferentially about the shaft. In other embodiments, a cutting device can include cutting members that vary in shape, size, spacing, and/or configuration. For example, in some embodiments, a cutting device can include a set of blades and a set of wires that collectively form the cutting members of the cutting device. In some embodiments, the diameter and/or size of the cutting members can vary. For example, in some embodiments, a cutting device can include wire cutting members that have decreasing diameter from a first diameter at a proximal end portion of the cutting member to a second diameter, substantially smaller than the first diameter, at the distal end portion. In still other embodiments, a cutting device can include one or more radio frequency cutting members, one or more laser cutting members, one or more ultrasonic cutting members, and/or any other suitable cutting members.

Figure 25:
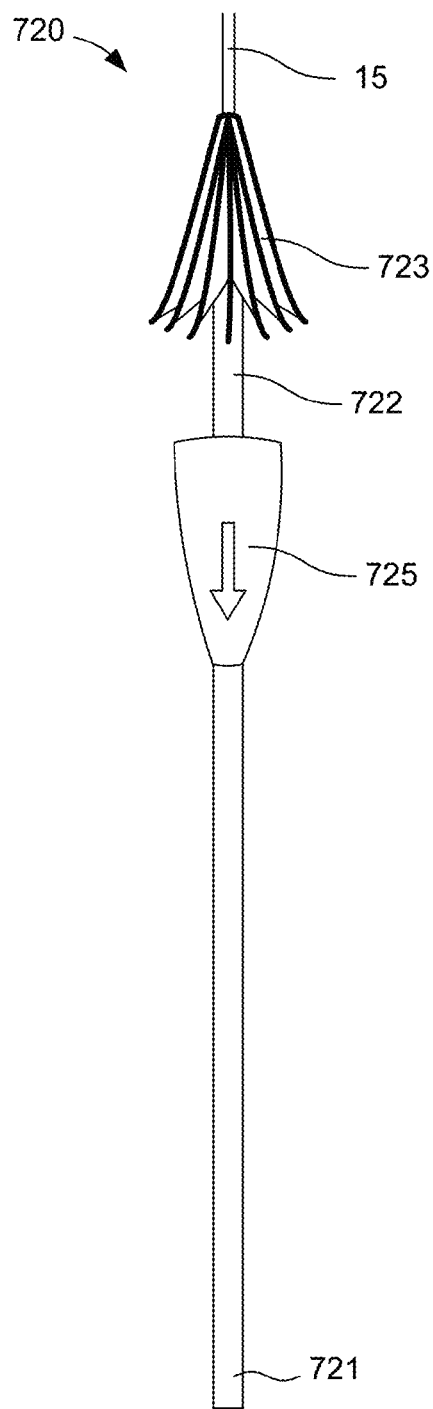
FIG. 25 is a schematic illustration of a cutting device in a first configuration, according to an embodiment.
Figure 26:
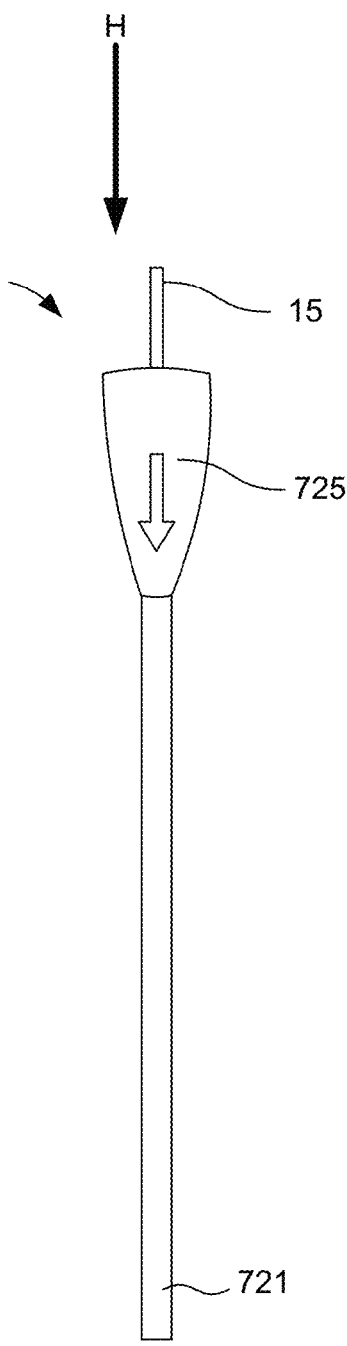
FIG. 26 is a schematic illustration of the cutting device of FIG. 25 in a second configuration.

In some embodiments, a cutting device can include, for example, a sheath, cover or the like that can be selectively disposed about at least a portion of a set of cutting members to reduce, for example, undesirable cutting of or contact with the anatomy. For example, FIGS. 25 and 26 illustrate a cutting device 720 disposed about a guide wire 15. The cutting device 720 can be substantially similar in form and/or function as the cutting device 520. As such, the cutting device 721 has a proximal end portion 721 and a distal end portion 722. The proximal end portion 721 can have and/or can be coupled to a user interface device, as described in detail above. The distal end portion 722 of the cutting device 720 includes and/or defines a set of cutting members 723. In some embodiments, the cutting members 723 can be substantially similar to or the same as the cutting members 523 described above with reference to FIG. 23. The cutting device 720 can differ from the cutting device 520, however, with the inclusion of a sheath 725. The sheath 725 can be any suitable device or member that is configured to be selectively placed about the cutting members 723. In some embodiments, the arrangement of the sheath 725 can be such that the sheath 725 substantially resists being cut by the cutting members 723. For example, in some embodiments, the sheath 725 can be formed from a material that is sufficiently hard to limit the cutting of the inner surface of the sheath 725 by the cutting members 723.

In some instances, the cutting device 720 can be inserted into, for example, an introducer catheter and/or the like to be disposed adjacent to the atrial wall. In some instances, the cutting members 723 can be at least partially disposed within the sheath 725 prior to cutting the atrial wall. In such instances, the sheath 725 can be retracted and/or the distal end portion 722 of the cutting device 720 can be advanced relative to the sheath 725 such that the sheath 725 no longer surrounds at least a portion of the cutting members 723. In this manner, the distal end portion 722 of the cutting device 720 can be advanced to cut the atrial wall, as described in detail herein. Although not shown in FIGS. 25 and 26, in some embodiments, the cutting device 720 can be used with any of the support devices 110, 210, 310, 410, and/or 510 described herein.

Once the atrial wall has been cut, the distal end portion 722 of the cutting device 720 can be retracted such that at least a portion of the cutting members 723 are again disposed in the sheath 725, as indicated by the arrow H in FIG. 26. In this manner, the cutting device 720 can be retracted through, for example, the introducer catheter and/or the like and removed from the body of a patient.

Although not shown in FIGS. 25 and 26, in some embodiments, the cutting members 723 can be configured to deform when disposed within the sheath 725. For example, in some embodiments, the cutting members 723 can be collapsible or bendable, and can be configured to transition from a first (or retraction) configuration in which the cutting members 723 are deformed and disposed in the sheath 725, to a second (or cutting) configuration in which the cutting members 723 are substantially expanded and are disposed outside of the sheath. In this manner, the cutting members 723 in the refraction configuration can have a size smaller than a size of the cutting members 723 in the cutting configuration. In use, such an arrangement allows for the cutting members 723 to be removed through the atrial wall 3 without undesirably increasing the size of or otherwise undesirably disturbing the opening in the atrial wall 3. In some embodiments, the cutting members 723 can be operably coupled to, for example, a wire or the like that can be operable in transitioning the cutting members 723 between the first configuration and the second configuration.

Any of the cutting devices described herein can be used to make an incision in the atrial wall through which a portion of an inlet flow cannula of a VAD can be disposed. For example, as shown in FIGS. 27-30, a cutting device 820 can have a distal end portion 822 that includes a set of cutting members 823. The cutting device 820 can be disposed about a guide wire 15 and advance along a length of the guide wire to make an incision in the atrial wall 3, as described in detail above. Once, the atrial wall is cut, a portion of an inlet flow cannula 23 can be inserted through the incision to be disposed within the atrium (e.g., the left atrium). In this manner and as described above with reference to FIGS. 2-5, the inlet flow cannula 23 can be manipulated to transition an end portion 24 (e.g., a trumpeted end portion) to an at least partially open configuration. Once opened, a user can manipulate a portion (not shown) of the cutting device 820 to transition the cutting members 823 between an undeformed configuration (e.g., a cutting or expanded configuration) and a deformed configuration (e.g., a refraction or collapsed configuration), as indicated by the arrow I in FIG. 28. In this manner, the cutting device 820 can be retracted through the inlet flow cannula 23 and the end portion 24 can be transitioned to a configuration suitable for coupling the end portion 24 to the atrial wall 3 (e.g., the trumpeted end portion is transitioned to a completely open configuration), as indicated by the arrow J in FIG. 29.

Figure 27:
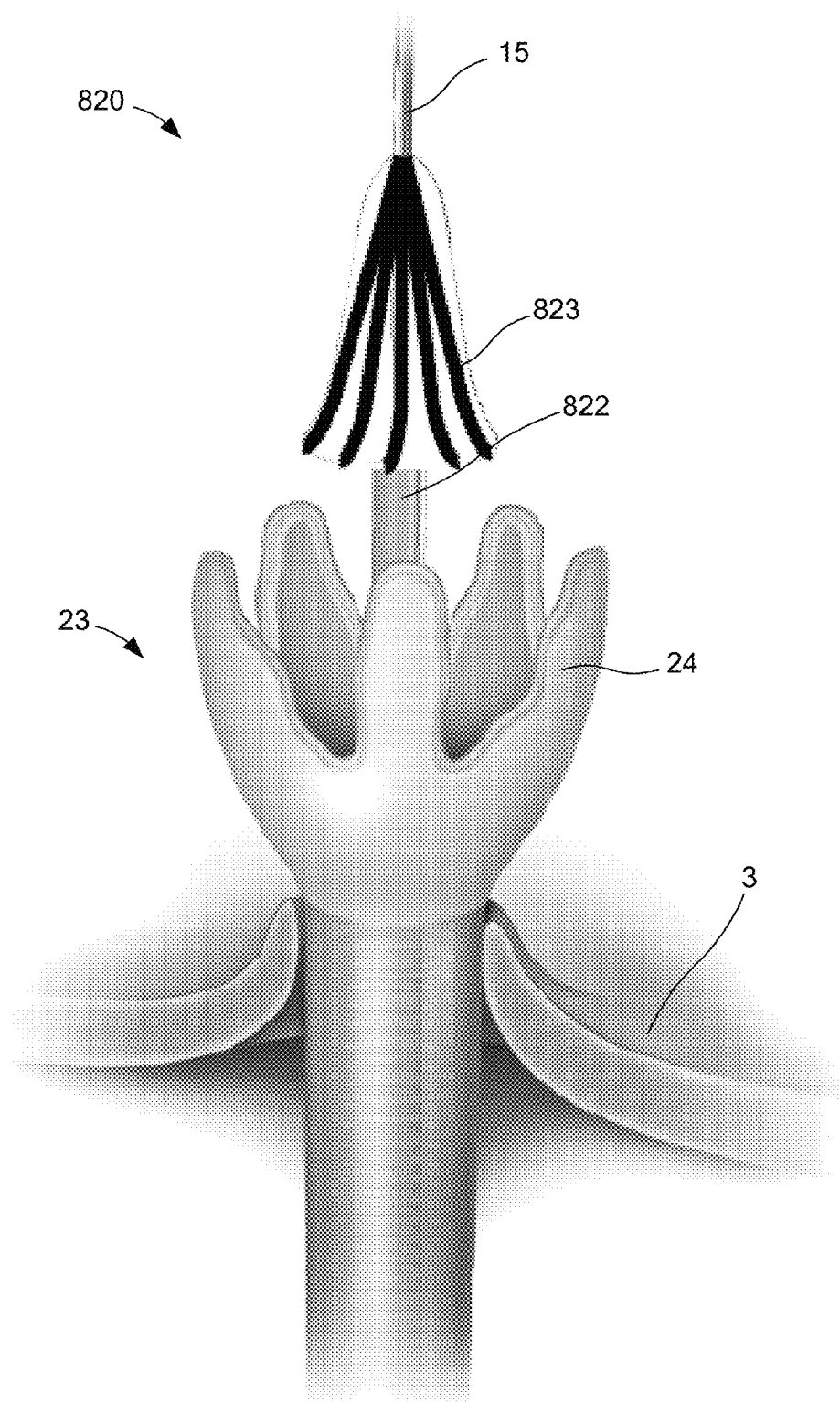
FIGS. 27-29 are schematic illustrations of a portion of a cutting device and a portion of an inlet flow cannula of a device in a first configuration, a second configuration, and a third configuration, respectively, according to an embodiment.
Figure 28:
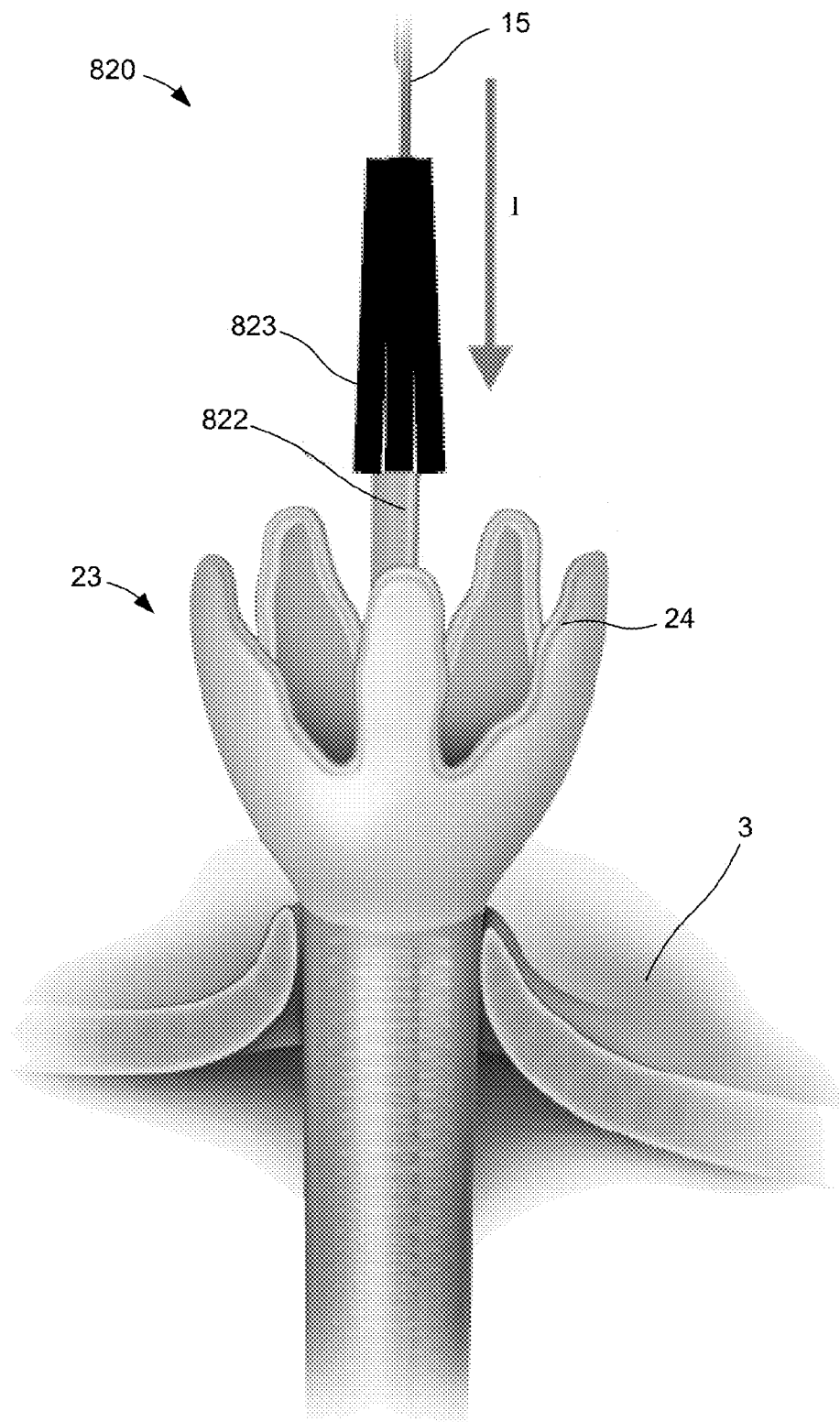
Figure 29:
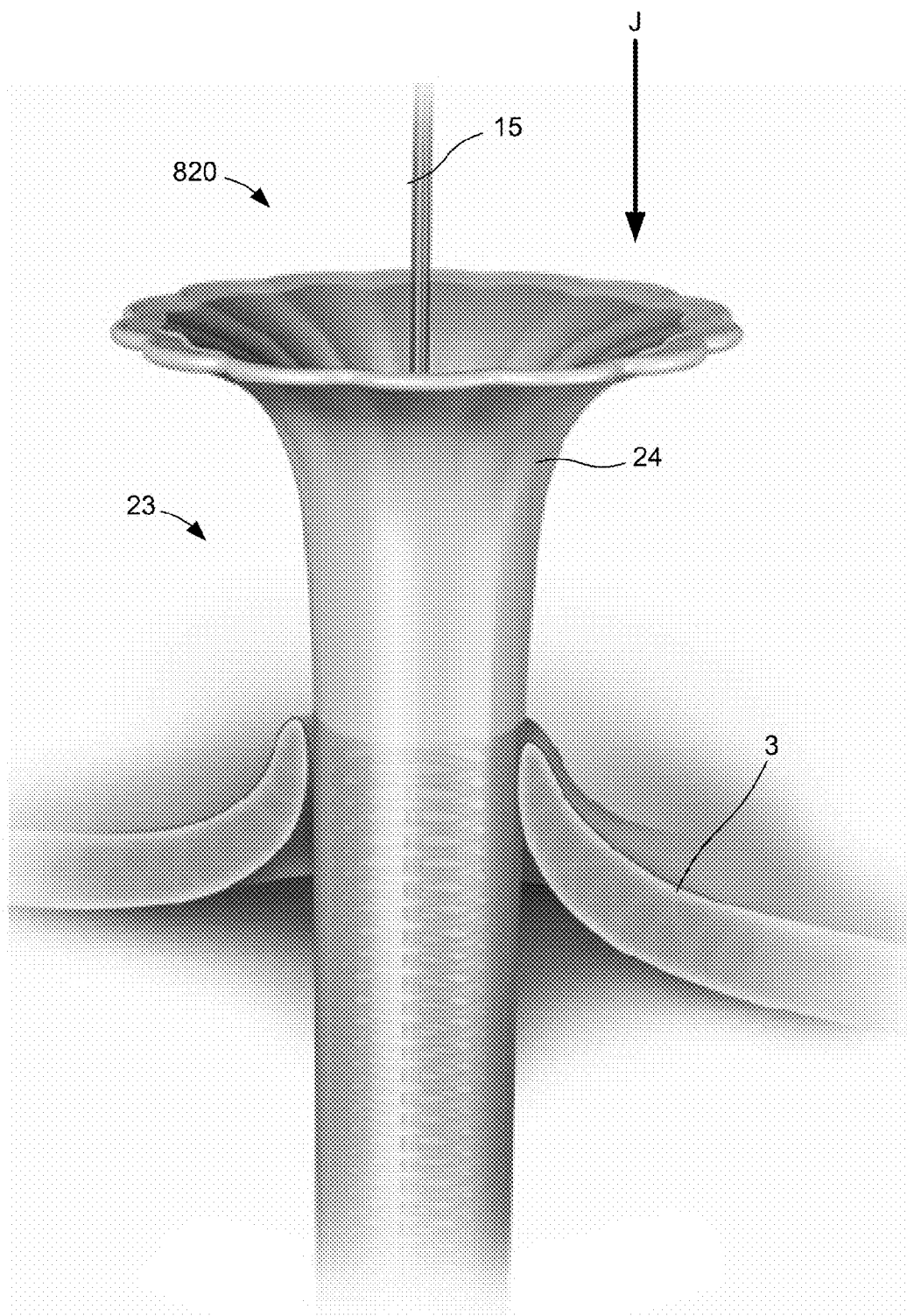

Although not shown in FIGS. 27-29, in some embodiments, the cutting device 820 can include and/or be otherwise coupled to a sheath or the like, as described in detail above with reference to FIGS. 25 and 26. In such embodiments, the sheath can be configured to substantially surround at least a portion of the cutting members 823 to reduce the possibility of cutting the inlet flow cannula 23 as the cutting device 820 is passed therethrough.

Figure 31:
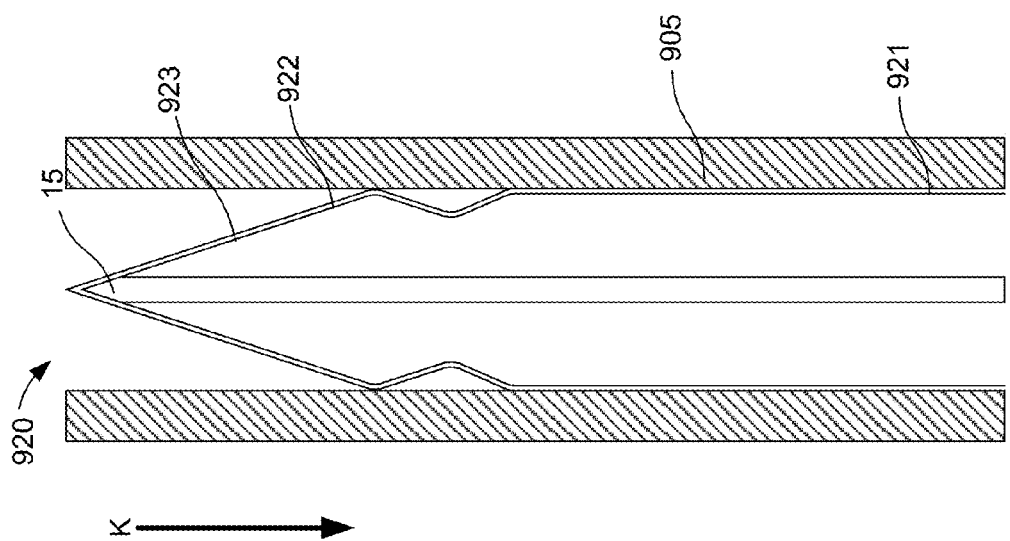
FIGS. 30 and 31 are side cross-sectional views of a cutting device in a first configuration and a second configuration, respectively, according to another embodiment.
Figure 30:
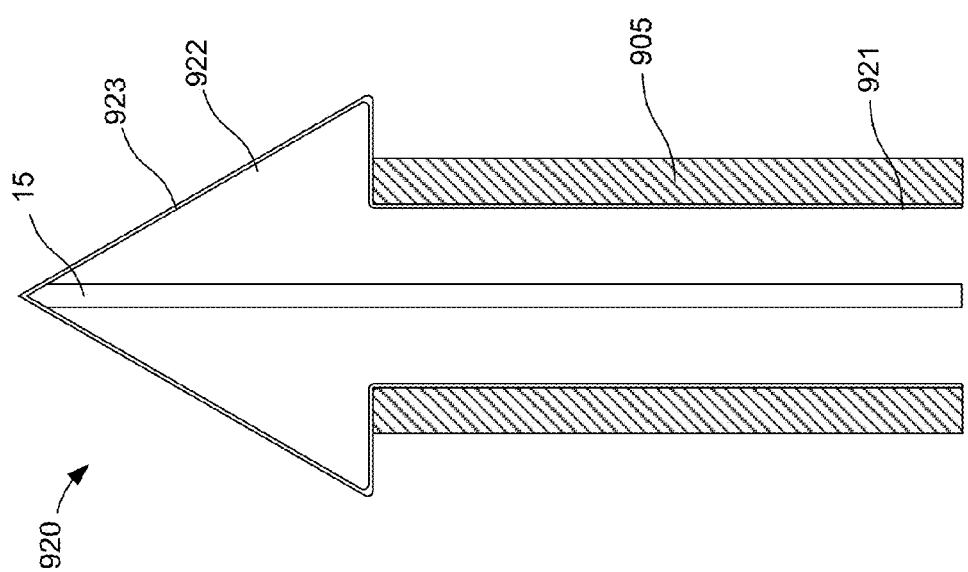

As described above, in some embodiments, a cutting device can be advanced through an introducer catheter to make an incision in the atrial wall. In some embodiments, the introducer catheter can be operable in transitioning the cutting device between a cutting configuration and a retraction configuration, as described above. For example, FIGS. 30 and 31 illustrate a cutting device 920 at least partially disposed within an introducer catheter 905. The cutting device 920 can be substantially similar in form and/or function as any of the cutting devices described herein. As such, the cutting device 920 has a proximal end portion 921 and a distal end portion 922. The proximal end portion 921 can include and/or can otherwise be coupled to a user interface device. The distal end portion 922 includes a cutting member 923 that can be transitioned between a first configuration (e.g., a cutting configuration) and a second configuration (e.g., an insertion and retraction configuration). The cutting member 923 can be substantially similar to or the same as any of the cutting members described herein. Moreover, as shown in FIGS. 30 and 31, the cutting device 920 can be disposed about a guide wire 15 or any of the support members shown and described herein.

In some instances, the cutting device 920 can be in the first configuration such that the cutting members 923 extend beyond a distal end surface of the introducer catheter. Although not shown in FIGS. 30 and 31, in some instances, a support member can be placed adjacent to the atrial wall to support the atrial wall during a cutting event. In this manner, the cutting device 920 can be advanced to place the cutting members 923 in contact with the atrial wall (not shown in FIGS. 30 and 31) and further advanced to make an incision in the atrial wall. Once an incision having a desired size and/or characteristic is defined in the atrial wall, a user can manipulate the proximal end portion 921 of the cutting device 920 to retract the cutting members 920 into the introducer catheter 905. Thus, the cutting members 923 are transitioned from the first configuration and the second configuration, as indicated by the arrow K in FIG. 31. With the cutting members 923 of the cutting device 920 retracted into the introducer catheter, the introducer catheter 905 can be, for example, retracted from the body.

Figure 32:
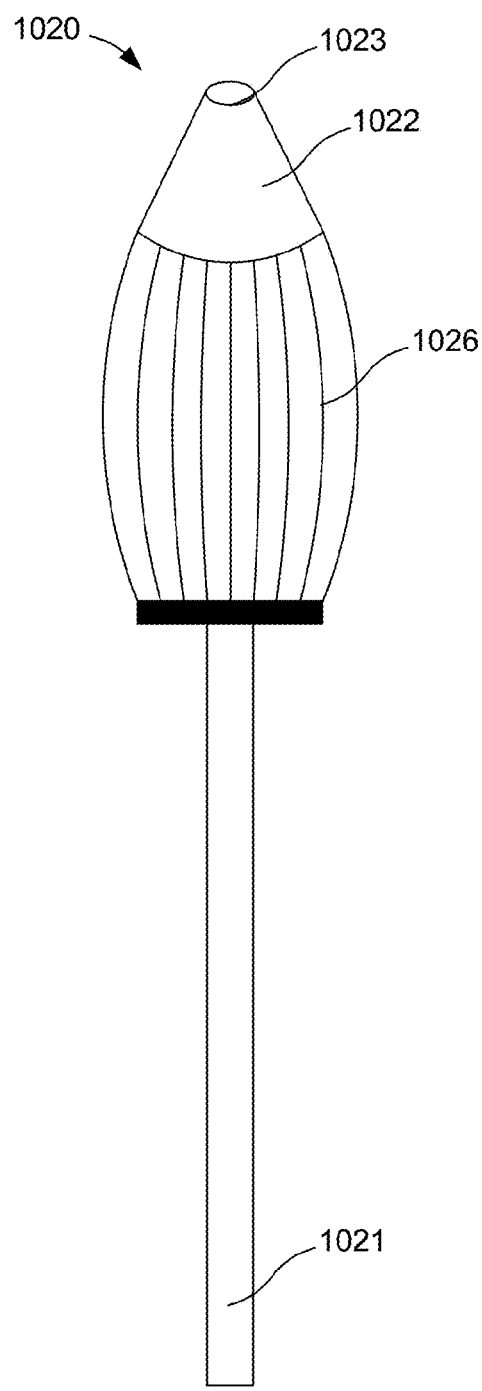
FIG. 32 is a schematic illustration of a cutting device according to another embodiment.

Although the distal end portions of the cutting devices 120, 420, 520, 620, 720, 820, and 920 have been shown as only including a cutting members 123, 423, 523, 623, 723, 823, and 923, respectively, in other embodiments, a cutting device can include any other suitable device and/or component that is disposed at the distal end portion of the cutting device. For example, FIG. 32 is a schematic illustration of a cutting device 1020 according to another embodiment. The cutting device 1020 has a proximal end portion 1021 and a distal end portion 1022. The proximal end portion 1021 can include and/or can be coupled to a user interface device, as described in detail above. The distal end portion 1022 includes a cutting member 1023 and a balloon catheter 1026. The cutting member 1023 can be, for example, an annular ring that can include a leading edge that is suitable for cutting and/or coring the atrial wall (not shown in FIG. 32). As shown, the cutting member 1023 can be configured to increase in diameter from a first diameter at the distal end portion of the cutting member 1023 to a second diameter, larger than the first diameter, at the proximal end portion of the cutting member 1023. In this manner, the size of the incision or core can be associated with the relative amount of the cutting member 1023 that is advanced through the atrial wall. Although not shown in FIG. 32, the cutting device 1020 can be used with, for example, a support member, such as any of those described herein.

The balloon catheter 1026 can be operably coupled to a fluid source that can be actuated to transition the balloon catheter 1026 between a first configuration (e.g., a deflated configuration) and a second configuration (e.g., an inflated configuration). For example, in some embodiments, the balloon catheter 1026 can be in fluid communication with an air source that can be operable in inflating the balloon catheter 1026. In this manner, the cutting members 1023 of the cutting device 1020 can cut or core the atrial wall and the balloon catheter 1026 can be inserted, at least partially, into the cut or core. In some instances, the balloon catheter 1026 can be inflated to dilate the cut or core to, for example, facilitate the insertion of a portion of an inlet flow cannula of a VAD or the like.

Figure 33:
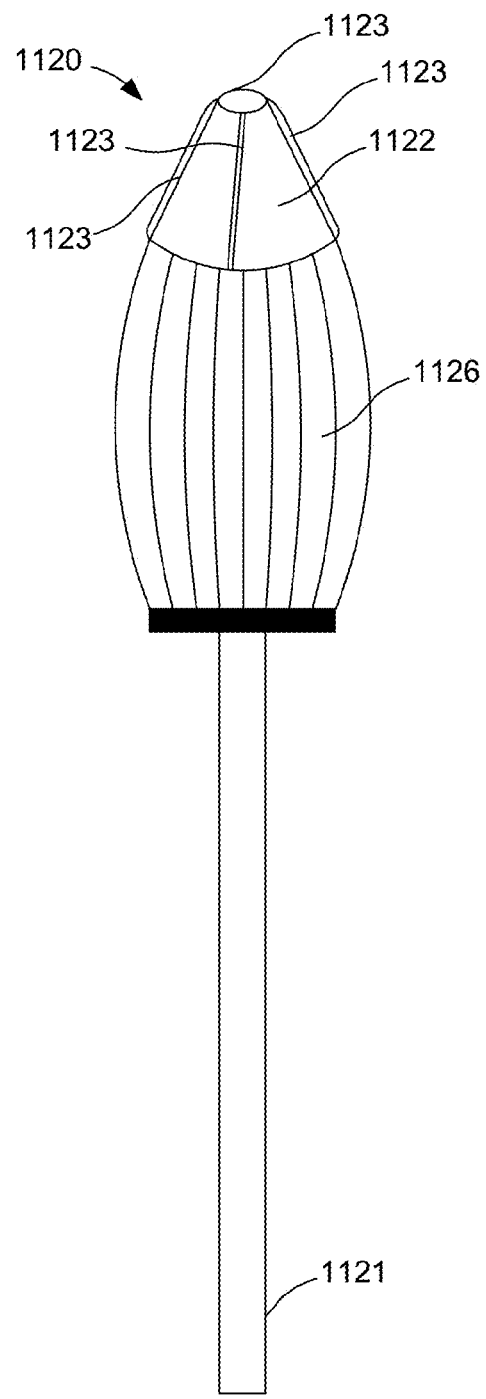
FIG. 33 is a schematic illustration of a cutting device according to another embodiment.

Although the cutting device 1020 is shown as including a single cutting member 1023, in other embodiments, a cutting device can include multiple cutting members. For example, FIG. 33 is an illustration of a cutting device 1120 according to another embodiment. The cutting device 1120 can be substantially similar in form and function as the cutting device 1020. As such, the cutting device 1120 has a proximal end portion 1121 that includes or that is coupled to a user interface device and a distal end portion 1122 that includes a set of cutting members 1123 and a balloon catheter 1126. As shown in FIG. 33, the cutting device 1120 can include a cutting member 1123 that is, for example, an annular ring that can include a leading edge that is suitable for cutting and/or coring the atrial wall (not shown in FIG. 33). The cutting device 1120 also includes a set of cutting members 1123 that extend from a surface of the distal end portion 1122 of the cutting device 1120. These cutting members 1123 can be, for example, blades or the like that can be configured to facilitate the insertion of the distal end portion 1122 of the cutting device 1120 through the atrial wall. The balloon catheter 1126 can be substantially similar in form and function as the balloon catheter 1026 included in the cutting device 1020 of FIG. 32. In this manner, the balloon catheter 1126 can be configured to dilate an incision or core made by the cutting members 1123 to facilitate, for example, the insertion of a portion of an inlet flow cannula of a VAD or the like.

Referring now to FIGS. 34 and 35, a cutting device can include any number of cutting members in any suitable arrangement or configuration. In this manner, the characteristics of an incision in the atrial wall can be, for example, accurate and repeatable with a limited amount of undesired tearing of the atrial wall. Similarly stated, the tools and methods described herein can be used to produce an incision that is resistant to tearing and/or has limited stress-concentration risers. For example, FIG. 34 illustrates an incision commonly made in an atrial wall using known techniques. As shown, the incision is a relatively long and substantially linear incision. In some instances, such an incision can lead to, for example, tears in the atrial wall due at least in part to the profile and/or characteristics of the incision. For example, the linear characteristic of the incision can lead to stress concentration risers at the ends of the incision that can lead to unwanted tearing of the atrial wall.

As shown in FIG. 35, a cutting device including any suitable cutting member arrangement can be configured to make an incision in the atrial wall having any suitable profile and/or characteristics. In some embodiments, the incision made by any of the cutting devices described herein can be configured to minimize unwanted tearing and/or the like due at least in part to reducing stress concentration risers, incising in multiple direction simultaneous, and/or the like.

Figure 36:
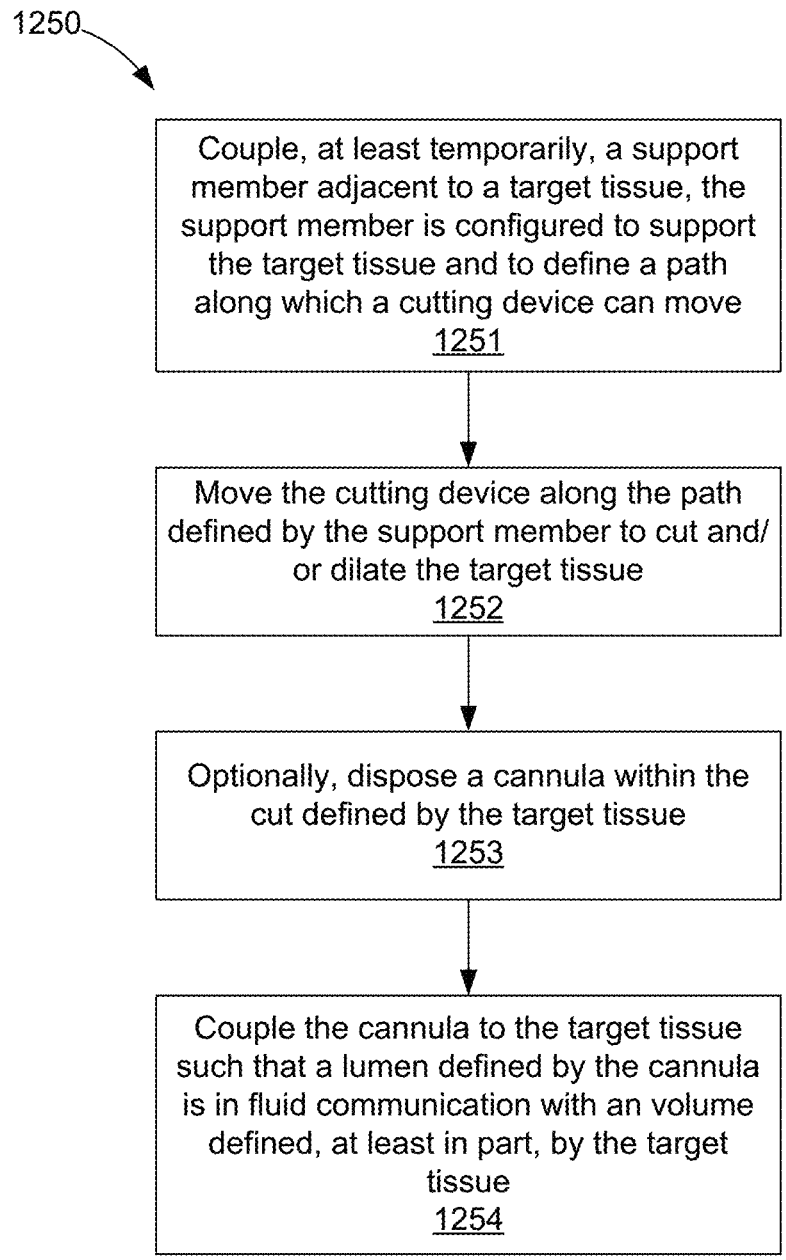
FIG. 36 is a flowchart illustrating a method of coupling a cannula to a target tissue according to an embodiment.

FIG. 36 is a flowchart illustrating a method 1250 of coupling, for example, an inlet flow cannula of a VAD to a wall of the heart, according to an embodiment. The method 1250 includes coupling, at least temporarily, a support member adjacent to a target tissue, at 1251. The support member is configured to support the target tissue and to define a path along which a cutting device can move. For example, in some embodiments, the support member can be a wire formed from a shape memory alloy such as Nitinol™. In such embodiments, the support member can be substantially similar to or the same as, for example, the support members 110 (FIGS. 6-14), 210 (FIG. 15), and/or 310 (FIG. 16). In this manner, a distal end portion of the support member can be transitioned between a first configuration and a second configuration to form, for example, a substantially annular ring that can be placed in contact with, for example, a surface of an atrial wall. The substantially annular ring formed by the distal end portion of the support member can be placed in contact with the atrial wall to limit an amount of deflection and/or deformation of the atrial wall when exposed to an external force.

The method 1250 includes moving the cutting device along the path defined by the support member to cut and/or dilate the target tissue, at 1252. For example, as described above with reference to the support member 110 of FIGS. 6-14, at least a portion of the of the support member can be a guide wire about which at least a portion of the cutting device can be disposed. In this manner, a user (e.g., a doctor, physician, surgeon, technician, etc.) can manipulate, for example, a proximal end portion of the cutting device to move the distal end portion. The distal end portion of the cutting device can include any of the cutting members described herein. Thus, the distal movement of the distal end portion of the cutting device places the cutting member in contact with a surface of, for example, the atrial wall such that further distal movement results in the cutting member incising the atrial wall. The incision (e.g., the cut) in the atrial wall formed by the cutting member can be any suitable shape and/or size in accordance with the shape, size, and/or relative positioning of the cutting member. For example, a cutting member can increase in size from a distal end portion to a proximal end portion and, therefore, a depth of the cutting member relative to the atrial wall can dictate, at least partially, the shape and/or size of the incision. In some instances, the cutting device can include and/or can be coupled to a device that can dilate the incision in the atrial wall.

With the incision formed in the target tissue (e.g., the atrial wall) and, in some instances, with the incision dilated, the method can optionally include disposing a cannula within the incision defined by the target tissue, at 1253. The cannula can be, for example, an inlet flow cannula of a VAD and/or any other suitable cannula. In some embodiments, the cannula can include a distal end portion that can be transitioned between a first, substantially closed configuration and a second, substantially open configuration. For example, the cannula can be in the first configuration when passed through the incision formed in the target tissue and once a desired portion of the cannula extends beyond the target tissue, the cannula can be transitioned to the second configuration. In some embodiments, the distal end portion of the cannula can be substantially trumpet-shaped when in the second configuration, as shown, for example, in FIGS. 2-5. In other embodiments, the cannula need not be disposed within the incision. For example, in some embodiments, the cannula can be placed in a desired position adjacent to the atrial wall such that a lumen defined by the cannula is in fluid communication with the incision. In some embodiments, the lumen defined by the cannula can substantially circumscribed the incision.

Once disposed in the desired configuration and/or placement relative to the target tissue, the cannula is coupled to the target tissue such that a lumen defined by the cannula is in fluid communication with a volume defined, at least in part, by the target tissue, at 1254. For example, in some embodiments, the cannula can be transitioned to a second, open configuration and can then be sutured to the atrial wall. In some instances, the support member can be in contact with the target tissue and configured to limit the amount of deflection and/or deformation of the atrial wall during suturing. In other embodiments, the cannula can be coupled to the target tissue via an adhesive or the like. In still other embodiments, the cannula can be coupled to the target tissue via a combination of any suitable mechanical fastening (e.g., sutures) and any suitable adhesive. In this manner, a lumen defined by, for example, an inlet flow cannula of a VAD can be placed in fluid communication with, for example, the left atrium of the heart to fluidically couple the VAD to the left atrium.

Figure 37:
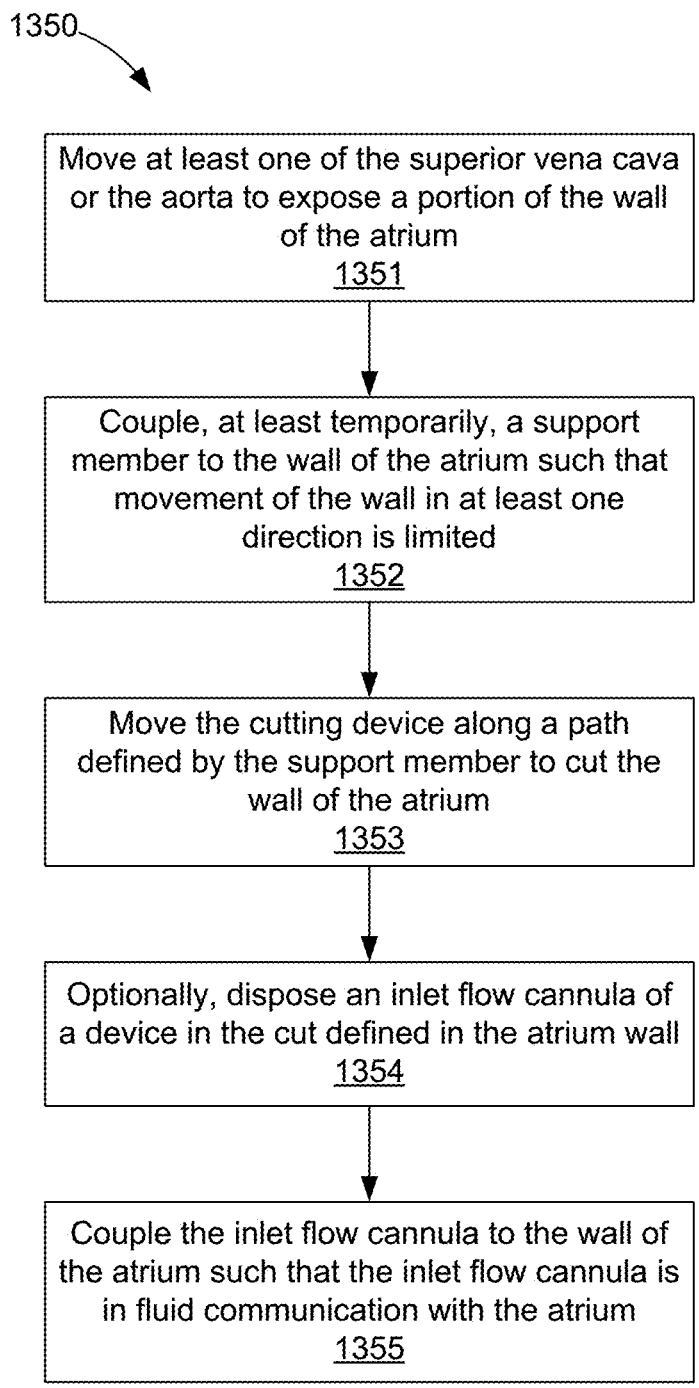
FIG. 37 is a flowchart illustrating a method of coupling a cannula to a target tissue according to another embodiment.

FIG. 37 is a flowchart illustrating a method 1350 of coupling, for example, an inlet flow cannula of a VAD to a wall of a left atrium of a heart, according to an embodiment. The method 1350 includes moving at least one of the superior vena cava or the aorta to expose a portion of the wall of the atrium, at 1351. For example, in some instances, a surgeon, doctor, or other practitioner can move at least a portion of the superior vena cava in a direction towards the heart (e.g., downward towards the heart and/or in a proximal direction towards the heart). In other instances, the surgeon, doctor, and/or the like can move at least a portion of the aorta in a direction away from the heart (e.g., upwards away from the heart and/or in a distal direction away from the heart and/or in a direction substantially opposite the superior vena cava). In still other instances, the surgeon, doctor, or other practitioner can move both the superior vena cava and the aorta in substantially opposite directions to expose the portion of the wall of the atrium. In some instances, moving at least a portion of the superior vena cava or the aorta to expose a portion of the wall of the atrium can be optional.

With the superior vena cava and/or the aorta moved to a desired position relative to the heart, a support member is at least temporarily coupled to the wall of the atrium such that movement of the wall in at least one direction is limited, at 1352. For example, as described above, the support member is configured to support the target tissue and to define a path along which a cutting device can move. For example, in some embodiments, the support member can be a wire formed from a shape memory alloy such as Nitinol™. In such embodiments, the support member can be substantially similar to or the same as, for example, the support members 110 (FIGS. 6-14), 210 (FIG. 15), and/or 310 (FIG. 16). In this manner, a distal end portion of the support member can be transitioned between a first configuration and a second configuration to form, for example, a substantially annular ring that can be placed in contact with, for example, a surface of an atrial wall. For example, in some instances, the distal end portion of the support member can be inserted, at least partially, through the atrial wall (e.g., the dome wall 3 of the left atrium 2 of the heart 1 in FIG. 1) and once disposed in the atrium, can be transitioned (e.g., via a application or removal of force, heat, current, and/or the like) from the first configuration to the second configuration to form the annular ring. The substantially annular ring formed by the distal end portion of the support member can be placed in contact with an interior surface of the atrial dome wall to limit an amount of deflection and/or deformation of the atrial dome wall when exposed to an external force.

The method 1350 includes moving the cutting device along the path defined by the support member to cut the wall of the atrium, at 1354. For example, as described above with reference to the support member 110 of FIGS. 6-14, at least a portion of the of the support member can be a guide wire about which at least a portion of the cutting device can be disposed. In other embodiments, the cutting device can be disposed within a lumen defined by a catheter and/or the like, as shown, for example, in FIGS. 18-20. In this manner, the surgeon, doctor, and/or the like can manipulate, for example, a proximal end portion of the cutting device to move the distal end portion. The distal end portion of the cutting device can include any of the cutting members described herein. Thus, the distal movement of the distal end portion of the cutting device places the cutting member in contact with an exterior surface of the atrial dome wall such that further distal movement results in the cutting member incising the atrial dome. The incision (e.g., the cut) in the atrial dome wall formed by the cutting member can be any suitable shape and/or size in accordance with the shape, size, and/or relative positioning of the cutting member, as described herein. In some embodiments, the cutting device can include and/or can be coupled to dilation member that can, for example, dilate the incision.

With the incision formed in the atrial wall, the inlet flow cannula of the VAD is optionally disposed within the incision defined by the atrial wall, at 1355. In some embodiments, the inlet flow cannula can be substantially similar to the inlet flow cannula 13 shown, for example, in FIGS. 2-5. In other embodiments, the inlet flow cannula need not be disposed within the incision. For example, in some embodiments, the inlet flow cannula can be placed in a desired position adjacent to the atrial wall such that a lumen defined by the inlet flow cannula is in fluid communication with the incision. In some embodiments, the lumen defined by the inlet flow cannula can substantially circumscribed the incision.

Once disposed in the desired configuration and/or placement relative to the atrial wall, the inlet flow cannula is coupled to the atrial wall such that the inlet flow cannula is in fluid communication with the atrium, at 1355. For example, in some embodiments, the inlet flow cannula can be transitioned to a second, open configuration and can then be sutured to the atrial wall, as described in detail herein. In this manner, the lumen defined by the inlet flow cannula of the VAD can be placed in fluid communication with the left atrium of the heart to fluidically couple the VAD to the left atrium.

Figure 38:
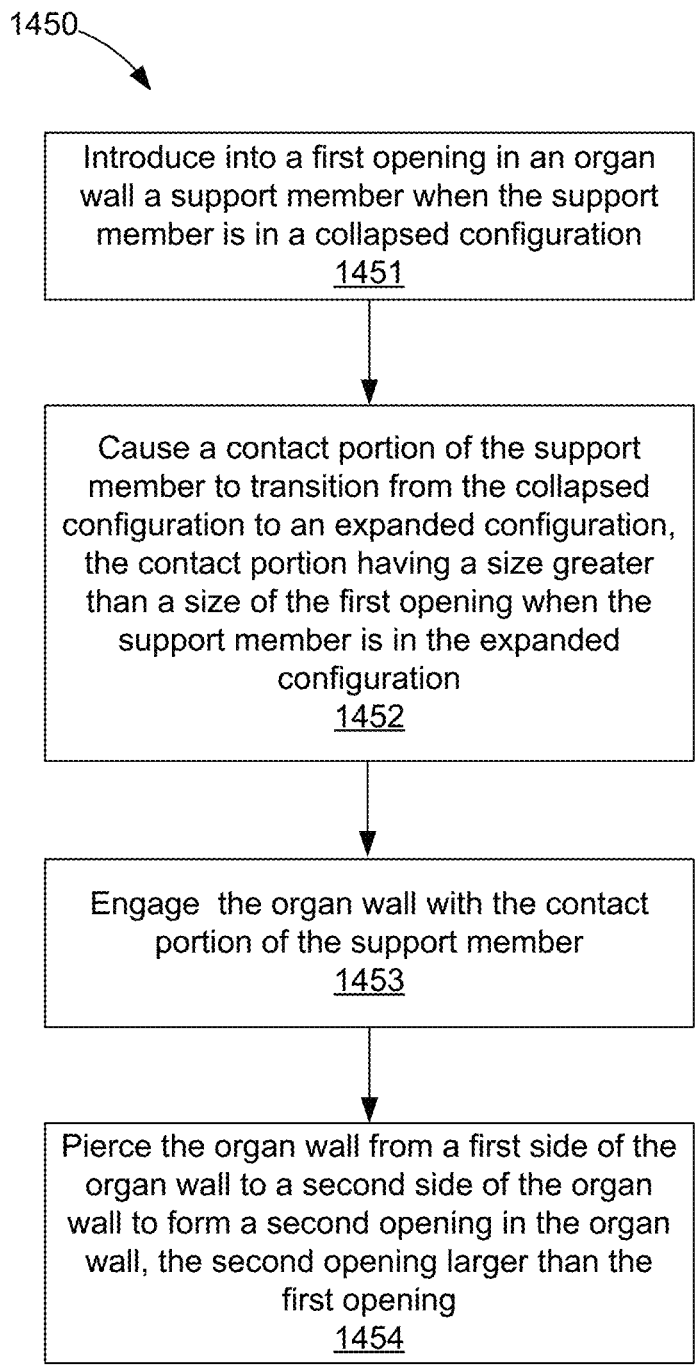
FIG. 38 is a flowchart illustrating a method of piercing an organ wall according to an embodiment.

FIG. 38 is a flowchart illustrating a method 1450 of piercing an organ wall, according to an embodiment. The method 1450 includes introducing into a first opening in an organ wall (e.g., atrial wall 3) a support member when the support member is in a collapsed configuration, at 1451. The support member, for example, can be a wire formed from a shape memory alloy such as Nitinol™. The support member can be substantially similar to or the same as, for example, the support members 110 (FIGS. 6-14), 210 (FIG. 15), and/or 310 (FIG. 16).

The method 1450 includes causing a contact portion of the support member to transition from the collapsed configuration to an expanded configuration, at 1452, and engaging an organ wall with the contact portion, at 1453. In this manner, the support member can be transitioned to form, for example, a substantially annular ring that can be placed in contact with, for example, a surface of an atrial wall. The substantially annular ring formed by the contact portion of the support member can be placed in contact with the organ wall (e.g., atrial wall 3) to limit an amount of deflection and/or deformation of the atrial wall when exposed to an external force, and/or promote a taut target portion (or surface) of the atrial wall for a piercing and/or cutting procedure. For example, as discussed in further detail herein, the contact portion of the support member can deform the atrial wall in a radial direction from the center point (e.g., the location at an external force may be applied).

The method 1450 includes piercing the organ wall from a first side of the organ wall to a second side of the organ to form a second opening in the organ wall that is larger than the first (or initial) opening, at 1454. In this manner, a user (e.g., a doctor, physician, surgeon, technician, etc.) can manipulate, for example, a cutting device to pierce and/or cut a portion of the atrial wall that is supported by the support member. The cutting device can include any of the cutting members described herein. The incision (e.g., the cut) in the atrial wall formed by the cutting member can be any suitable shape and/or size in accordance with the shape, size, and/or relative positioning of the cutting member. For example, a cutting member can increase in size from a distal end portion to a proximal end portion and, therefore, a depth of the cutting member relative to the atrial wall can dictate, at least partially, the shape and/or size of the incision. In some instances, the cutting device can include and/or can be coupled to a device that can dilate the incision in the atrial wall.

For example, in some embodiments, the contact portion 112 can deform the atrial wall 3 (or any suitable organ wall) in a radial direction from the center point (i.e., away from where a puncture member or support member penetrates, punctures, or otherwise applies pressure to). In this manner, the atrial wall 3 can be moved into and/or held in a preferable position or configuration when a cutting force or pressure is applied thereto. In some instances, this can reduce the puncturing forces to penetrate the atrial wall 3. In some instances, the "stretching" of the atrial wall 3 can minimize and/or eliminate any "bunching" of the atrial wall 3 that may otherwise occur, and instead can produce a surface layer having a substantially constant thickness. In this manner, the contact portion 112 can cause movement of and/or stabilize at least a portion of the atrial wall 3 such that at least the portion of the atrial wall 3 is in a preferable position during the piercing and/or cutting.

Figure 39:
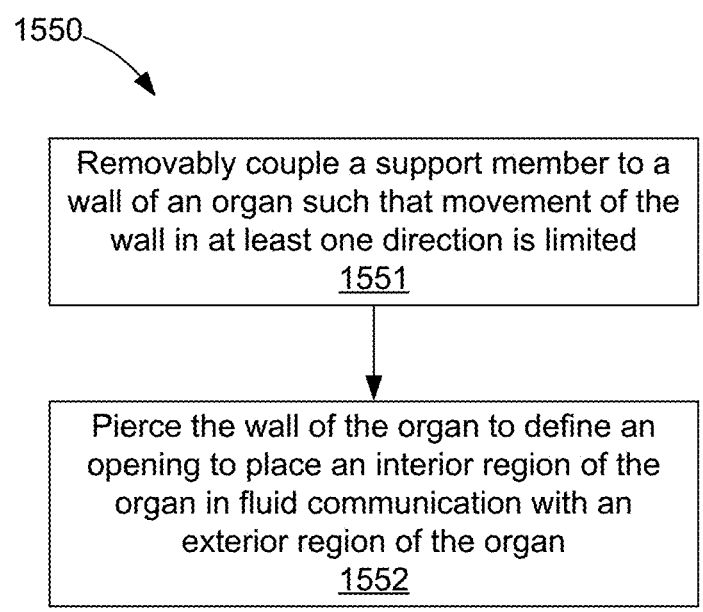
FIG. 39 is a flowchart illustrating a method of piercing an organ wall according to another embodiment.

FIG. 39 is a flowchart illustrating a method 1550 of piercing an organ wall, according to an embodiment. The method 1550 includes removably coupling a support member to a wall of an organ (e.g., atrial wall 3), at 1551, such that movement of the wall in at least one direction is limited. In this manner, the support member can be placed in contact with the atrial wall to limit an amount of deflection and/or deformation of the atrial wall when exposed to an external force, and/or promote a taut target portion (or surface) of the atrial wall for a piercing and/or cutting procedure. The support member, for example, can be a wire formed from a shape memory alloy such as Nitinol™. The support member can be substantially similar to or the same as, for example, the support members 110 (FIGS. 6-14), 210 (FIG. 15), and/or 310 (FIG. 16).

The method 1550 includes piercing the wall of the organ to define an opening to place an interior region of the organ in fluid communication with an exterior region of the organ, at 1552. In this manner, a user (e.g., a doctor, physician, surgeon, technician, etc.) can manipulate, for example, a cutting device to pierce and/or cut a portion of the atrial wall that is supported by the support member. The cutting device can include any of the cutting members described herein. The incision (e.g., the cut) in the atrial wall formed by the cutting member can be any suitable shape and/or size in accordance with the shape, size, and/or relative positioning of the cutting member. For example, a cutting member can increase in size from a distal end portion to a proximal end portion and, therefore, a depth of the cutting member relative to the atrial wall can dictate, at least partially, the shape and/or size of the incision. In some instances, the cutting device can include and/or can be coupled to a device that can dilate the incision in the atrial wall.

In some embodiments, an apparatus includes a support member configured to be transitioned between a first configuration and a second configuration. When the support member is in the first configuration a contact portion of the support member is configured to be inserted through an organ wall from a first side of the organ wall to a second side of the organ wall. When the support member is in the second configuration the contact portion of the support member is configured to contact the second side of the organ wall to limit movement of the organ wall. The contact portion of the support member has a first size when the support member is in the first configuration and a second size when the support member is in the second configuration, the second size being larger than the first size. The support member has a guide portion including a surface along which a puncture member can be slidably disposed. The puncture member is configured to puncture the organ wall when the puncture member is moved along the surface and when the support member is in the second configuration.

In some embodiments, a method includes introducing into a first opening in an organ wall a support member when the support member is in a collapsed configuration. After the introducing, a contact portion of the support member is transitioned from the collapsed configuration to an expanded configuration. The contact portion has a size greater than a size of the first opening when the support member is in the expanded configuration. The contact portion of the support member engages the organ wall. The organ wall is pierced from a first side of the organ wall to a second side of the organ wall to form a second opening in the organ wall, the second opening larger than the first opening.

In some embodiments, a method includes removably coupling a support member to a wall of an organ such that movement of the wall in at least one direction is limited. The wall of the organ is pierced to define an opening to place an interior region of the organ in fluid communication with an exterior region of the organ.

In some embodiments, an apparatus includes a support member having an outer catheter and an inner catheter at least partially disposed in a lumen defined by the outer catheter. The inner catheter and the outer catheter collectively define a vacuum channel therebetween. The support member is configured to be operably coupled to a vacuum source such that the vacuum source is placed in fluid communication with the vacuum channel. A contact portion of the support member is configured to be coupled to an organ wall when a suction force is produced within the vacuum channel by the vacuum source. The inner catheter defines a lumen configured to receive a puncture member such that the puncture member can be placed in contact with a target portion of the organ wall. The target portion is disposed within a region defined by the inner catheter.

In some embodiments, an apparatus includes a puncture member including multiple cutting members. A distal end portion of each cutting member is coupled together to form a cutting edge. The cutting members are configured to be transitioned between a cutting configuration and a retraction configuration. When the cutting members are in the cutting configuration, the cutting members collectively have a first size and are configured to pierce a target tissue to form an opening. When the cutting members are in the retraction configuration the cutting members collectively have a second size and are configured to be withdrawn through the opening, the first size being greater than the second size.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. Similarly, where methods and/or events described above indicate certain events and/or procedures occurring in certain order, the ordering of certain events and/or procedures may be modified. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above. For example, in some embodiments, a support device can include a first portion that is substantially similar to the support device 410 in FIGS. 17-20 and a second portion that is substantially similar to the support device 110 in FIGS. 6-14. In such embodiments, the first portion of the support device can be configured to exert a suction force on an outer surface of an atrial wall, while the second portion of the support device can be placed in contact with an inner surface of the atrial wall to provide mechanic and/or structural support.

What is claimed:

1. An apparatus, comprising:
a support member configured to be transitioned between a first configuration and a second configuration, when the support member is in the first configuration a contact portion of the support member is configured to be inserted through an organ wall from a first side of the organ wall to a second side of the organ wall, when the support member is in the second configuration the contact portion of the support member is configured to contact the second side of the organ wall to limit movement of the organ wall, the contact portion of the support member having a first size when the support member is in the first configuration and a second size when the support member is in the second configuration, the second size larger than the first size,
the support member having a guide portion including a surface configured to slideably receive a puncture member slidably coupled thereto, and when the support member is in the second configuration, the puncture member is configured to puncture the organ wall when the puncture member is moved along the surface and the support member substantially surrounds the guide portion, the puncture member further configured to be transitioned from a first puncture configuration to a second puncture configuration, when the puncture member is in the first puncture configuration the puncture member has a first diameter and is arranged to puncture the first side of the organ wall to produce an opening, when the puncture member is in the second puncture configuration the puncture member has a second diameter smaller than the first diameter and a diameter of the opening in the organ wall.

2. The apparatus of claim 1, wherein when the support member is in the second configuration, the contact portion of the support member forms a substantially annular ring substantially orthogonally to the guide portion.

3. The apparatus of claim 1, wherein a distal tip of the contact portion of the support member is configured to pierce the organ wall.

4. The apparatus of claim 1, wherein: when the support member is in the first configuration, the contact portion of the support member is substantially linear; and when the support member is in the second configuration, the contact portion of the support member is non-linear.

5. The apparatus of claim 1, further comprising: an actuator configured to be slidably coupled to the guide portion of the support member, the actuator configured to cause the puncture member to transition between the first puncture configuration and the second puncture configuration.

6. The apparatus of claim 1, wherein a portion of the guide portion of the support member is circumscribed by the contact portion of the support member when the support member is in the second configuration.

7. The apparatus of claim 1, wherein the guide portion of the support member extends on either side of the contact portion when the support member is in the second configuration.

8. A method, comprising:
introducing into a first opening in an organ wall a support member when the support member is in a collapsed configuration, the support member having a contact portion;
causing, after the introducing, the contact portion of the support member to transition from the collapsed configuration to an expanded configuration, the support member substantially surrounding a portion of itself when in the expended configuration, the contact portion having a size greater than a size of the first opening when the support member is in the expanded configuration;
engaging the organ wall with the contact portion;
piercing the organ wall from a first side of the organ wall to a second side of the organ wall to form a second opening in the organ wall, the second opening larger than the first opening; and
prior to the piercing, at least partially withdrawing the support member in the expanded configuration such that the contact portion of the support member contacts a surface of the organ wall.

9. The method of claim 8, wherein: the organ is a heart, the first side of the organ wall is an external surface of any one of the heart or a chamber therein, the second side of the organ wall is an internal surface of any one of the heart or the chamber therein.

10. The method of claim 8, wherein: the support member has a guide portion, and the piercing includes piercing the organ wall along an axis defined by the guide portion of the support member.

11. The method of claim 10, wherein: the piercing includes moving about the guide portion of the support member a puncture member from the first side of the organ to the second side of the organ to form the second opening in the organ.

12. The method of claim 11, wherein the puncture member is in a first puncture configuration during the piercing, the puncture member having a first diameter when the puncture member is in the first puncture configuration, the method further comprising:
causing, after the piercing and when the puncture member is disposed on the second side of the organ, the puncture member to transition from the first puncture configuration to a second puncture configuration, when the puncture member is in the second puncture configuration the puncture member has a second diameter smaller than (1) the first diameter, and (2) the second opening in the organ; and
moving the puncture member when the puncture member is in the second puncture configuration from the second side of the organ to the first side of the organ and through the second opening in the organ.

13. An apparatus, comprising: a support member having an outer catheter and an inner catheter at least partially disposed in a lumen defined by the outer catheter, the inner catheter and the outer catheter collectively defining a vacuum channel therebetween, the support member configured to be operably coupled to a vacuum source such that the vacuum source is placed in fluid communication with the vacuum channel, a contact portion of the support member configured to be coupled to an organ wall when a suction force is produced within the vacuum channel by the vacuum source, and the inner catheter defining a lumen configured to receive a puncture member such that the puncture member can be placed in contact with a target portion of the organ wall, the target portion being disposed within a region defined by the inner catheter; and the inner catheter and the outer catheter each having a proximal end portion and a distal end portion, the respective distal end portions having an outer diameter greater than an outer diameter of the respective proximal end portions, the distal end portions and the suction force configured to collectively move and hold in place the target portion of the organ wall while a cutting force is applied to the target portion of the organ wall by the puncture member.

14. The apparatus of claim 13, wherein: the contact portion is configured to operably cooperate with the suction force to apply tension to the target portion suitable to limit movement in at least one direction of the target portion.

* * * * *